US008066687B2

(12) United States Patent
Ashton et al.

(10) Patent No.: US 8,066,687 B2
(45) Date of Patent: Nov. 29, 2011

(54) SIDE SEAM FOR DISPOSABLE GARMENT

(75) Inventors: Gregory Ashton, Cincinnati, OH (US); Mary Elizabeth Davis, Madeira, OH (US); Alan John Edward Cucknell, Cambridgeshire (GB); Colin Dennis Ager, Cambridgeshire (GB); Robert James Wilkinson, Cambridgeshire (GB)

(73) Assignee: The Procter & Gamble Company, Cincinnati, OH (US)

( * ) Notice: Subject to any disclaimer, the term of this patent is extended or adjusted under 35 U.S.C. 154(b) by 920 days.

(21) Appl. No.: 11/541,325

(22) Filed: Sep. 29, 2006

(65) Prior Publication Data
US 2007/0073261 A1  Mar. 29, 2007

Related U.S. Application Data

(60) Provisional application No. 60/721,685, filed on Sep. 29, 2005.

(51) Int. Cl.
*A61F 13/15* (2006.01)
(52) U.S. Cl. ........ 604/396; 604/386; 604/387; 604/389; 604/393; 604/394
(58) Field of Classification Search .................. 604/396, 604/386, 387, 389, 393, 394
See application file for complete search history.

(56) References Cited

U.S. PATENT DOCUMENTS

| 2,075,189 A | 3/1937 | Galligan |
| 3,025,199 A | 3/1962 | Harwood |
| 3,860,003 A | 1/1975 | Buell |
| 3,911,173 A | 10/1975 | Sprague, Jr. |
| 3,929,135 A | 12/1975 | Thompson |
| 4,107,364 A | 8/1978 | Sisson |
| 4,209,563 A | 6/1980 | Sisson |
| 4,324,246 A | 4/1982 | Mullane et al. |
| 4,342,314 A | 8/1982 | Radel et al. |
| 4,463,045 A | 7/1984 | Ahr et al. |
| 4,515,595 A | 5/1985 | Kievit et al. |
| 4,573,986 A | 3/1986 | Minetola et al. |
| 4,610,678 A | 9/1986 | Weisman et al. |
| 4,610,681 A * | 9/1986 | Strohbeen et al. ............ 604/396 |

(Continued)

FOREIGN PATENT DOCUMENTS

EP    0657153 A2    6/1995
(Continued)

OTHER PUBLICATIONS

International Search Report, mailed Sep. 3, 2007, 4 pages.
(Continued)

*Primary Examiner* — Jacqueline F Stephens
(74) *Attorney, Agent, or Firm* — Charles R. Ware

(57) ABSTRACT

The present invention relates to a disposable absorbent article comprising a chassis defining a front waist region, a rear waist region, and a crotch region disposed between the front waist region and rear waist region. The article includes front and back ear panels that are joined at opposing side seams. The side seam can include an initiation region, which can be bonded or unbonded, and a propagation region. The initiation region and the propagation region have a resistance to user-applied opening forces. The resistance at the initiation region is less than that of the propagation region. The seam can further include additional regions. The article can include a tab member that can be engaged by the user to facilitate opening of the seam.

46 Claims, 27 Drawing Sheets

U.S. PATENT DOCUMENTS

| | | | |
|---|---|---|---|
| 4,673,402 A | 6/1987 | Weisman et al. | |
| 4,695,278 A | 9/1987 | Lawson | |
| 4,704,115 A | 11/1987 | Buell | |
| 4,785,996 A | 11/1988 | Ziecker et al. | |
| 4,795,454 A | 1/1989 | Dragoo | |
| 4,834,735 A | 5/1989 | Alemany et al. | |
| 4,834,741 A | 5/1989 | Sabee | |
| 4,842,666 A | 6/1989 | Werenicz | |
| 4,888,231 A | 12/1989 | Angstadt | |
| 4,909,803 A | 3/1990 | Aziz et al. | |
| 4,940,464 A | 7/1990 | Van Gompel et al. | |
| 4,988,344 A | 1/1991 | Reising et al. | |
| 4,988,345 A | 1/1991 | Reising | |
| 5,006,394 A | 4/1991 | Baird | |
| 5,143,679 A | 9/1992 | Weber et al. | |
| 5,147,345 A | 9/1992 | Young et al. | |
| 5,151,092 A * | 9/1992 | Buell et al. | 604/385.3 |
| 5,156,793 A | 10/1992 | Buell et al. | |
| 5,163,932 A | 11/1992 | Nomura et al. | |
| 5,167,897 A | 12/1992 | Weber et al. | |
| 5,169,932 A | 12/1992 | Raufman | |
| 5,171,239 A | 12/1992 | Igaue et al. | |
| 5,190,563 A | 3/1993 | Herron et al. | |
| 5,234,423 A | 8/1993 | Alemany et al. | |
| 5,246,433 A | 9/1993 | Hasse et al. | |
| 5,260,345 A | 11/1993 | DesMarais et al. | |
| 5,330,458 A | 7/1994 | Buell et al. | |
| 5,387,209 A | 2/1995 | Yamamoto et al. | |
| 5,397,316 A | 3/1995 | LaVon et al. | |
| 5,569,234 A | 10/1996 | Buell et al. | |
| 5,625,222 A | 4/1997 | Yoneda et al. | |
| 5,855,574 A * | 1/1999 | Kling et al. | 604/392 |
| 6,120,487 A | 9/2000 | Ashton | |
| 6,213,991 B1 * | 4/2001 | Kling et al. | 604/385.01 |
| 6,302,871 B1 | 10/2001 | Nakao et al. | |
| 6,443,940 B1 | 9/2002 | Ashton | |
| 6,607,515 B2 * | 8/2003 | Glaug et al. | 604/385.01 |
| 6,764,475 B1 | 7/2004 | Olson | |
| 2002/0032427 A1 | 3/2002 | Schmitz et al. | |
| 2003/0120240 A1 | 6/2003 | Buell et al. | |
| 2003/0216706 A1 | 11/2003 | Olsson et al. | |
| 2004/0162536 A1 | 8/2004 | Becker et al. | |

FOREIGN PATENT DOCUMENTS

| | | |
|---|---|---|
| EP | 0797968 A1 | 10/1997 |
| EP | 0839507 A | 6/1998 |
| EP | 1600132 A | 11/2005 |
| JP | 04-044920 | 4/1992 |
| WO | WO 96/31176 | 10/1996 |
| WO | WO 98/53780 A | 12/1998 |
| WO | WO01/21126 | 3/2001 |
| WO | WO 02/17843 A2 | 3/2002 |

OTHER PUBLICATIONS

U.S. Appl. No. 11/083,606, filed Mar. 18, 2005—Roe, et al.
U.S. Appl. No. 11/083,607, filed Mar. 18, 2005—Roe, et al.
U.S. Appl. No. 08/816,106, filed Mar. 14, 1997—Curro, et al.

* cited by examiner

SIDE SEAM FOR DISPOSABLE GARMENT

CROSS-REFERENCE TO RELATED APPLICATIONS

This application claims the benefit of U.S. Provisional Application No. 60/721,685 filed on Sep. 29, 2005, the substance of which is incorporated herein by reference.

FIELD OF INVENTION

This invention relates to disposable absorbent articles, and in particular relates to disposable garments having a reliable side seam that is easily opened by to remove the garment from the wearer.

BACKGROUND OF THE INVENTION

Infants and other incontinent individuals wear disposable garments such as diapers to receive and contain urine and other body exudates. Disposable pull-on garments, having fixed closed sides, have become popular for use on children who are able to walk and often who are toilet training. These pull-on garments have ear panels with edges that are seamed together, or otherwise pre-fastened, to form two encircled leg openings and an encircled waist opening.

In order to suitably contain body exudates as well as fit a wide variety of body shapes and sizes, pull-on garments need to fit snugly about the waist and legs of the wearer without drooping, sagging, or sliding down from its position on the torso. Examples of such pull-on garments are disclosed, for example, in U.S. Pat. No. 5,171,239 issued to Igaue et al. on Dec. 15; 1992, U.S. Pat. No. 4,610,681 issued to Strohbeen et al. on Sep. 9, 1986; U.S. Pat. No. 4,940,464 issued to Van Gompel et al. on Jul. 10, 1990; U.S. Pat. No. 5,246,433 to issued Hasse et al. on Sep. 21, 1993; U.S. Pat. No. 5,569,234 issued to Buell et al. on Oct. 29, 1996; and WO 96/31176 (Ashton) published on Oct. 10, 1996.

Proper fit of pull-on garments can be achieved when the garment applies an appropriate force to the lower torso region of the wearer. Such forces can be achieved using, for instance, a stretchable chassis that expands over the wearer's torso region as the garment is applied to the wearer. The shear and/or tensile forces resulting from the stretched chassis are applied to the side seams as the diaper is worn, and are exacerbated by wearer movement during use. As a result, the side seams need to be sufficiently strong so as to withstand these forces. At the same time, the side seams should fail predictably in response to a user-applied opening force when the article is to be removed from the wearer.

Unfortunately, the strength requirements to maintain integrity during use prevents conventional side seams from reliably and predictably failing in response to user-applied opening forces. As a result, when the user attempts to open the side seam open (e.g., for the purposes removing the garment), portions of the diaper surrounding the side seam may instead tear or fail in an unpredictable manner.

Moreover, conventional garments do not provide the user with any useful indication as to how to most easily open the seam. As a result, while the side seam is configured to be opened by the user, many users do not recognize this and instead tear the chassis itself, or an ear panel area that can be attached to the chassis, when removing soiled garments from the wearer.

What is therefore needed is a side seam for an absorbent article that is sufficiently robust to withstand the forces typically experienced during use, yet configured to reliably open in a predictable manner when the garment is to be removed from the wearer. It would be further desirable to provide a visual indicator on the garment that the user can identify as providing intuitive seam opening.

BRIEF SUMMARY OF THE INVENTION

The present invention provides a disposable pull-on garment having a pair of ear panels that are joined at opposing side seams to define a waist opening and a pair of leg openings. The side seams are configured to open reliably and predictably when desired.

In accordance with one aspect of the present invention, a disposable garment defines a front waist region, a back waist region, and a crotch region disposed between the front waist region and the back waist region. The garment includes a chassis that defines laterally opposing first and second side edges extending along the front waist region, the crotch region, and the back waist region. At least one of the side edges is joinable to itself by a seam at the front and back waist regions, respectively, to form a closed side interface defining a leg opening located at a lower end of the closed side interface, and at least partially defining a waist opening at an upper end of the closed side interface. An unseamed gap extends a distance between 4 mm and 50 mm substantially downward from the waist opening along a direction of elongation defined by the closed side interface.

In accordance with another aspect of the present invention, a disposable garment defines a front waist region, a back waist region, and a crotch region disposed between the front waist region and the back waist region. The garment includes a chassis defining laterally opposing first and second side edges extending along the front waist region, the crotch region, and the back waist region. At least one of the side edges is joined to itself by a seam at the front and back waist regions, respectively, to form a closed side interface defining a leg opening located at a lower end of the closed side interface, and at least partially defining a waist opening at an upper end of the closed side interface. The seam comprises an initiation region disposed above a propagation region. The initiation region has a resistance to a user-applied opening force that is less than that of the propagation region. The initiation region defines a vertical distance ratio within a range of 4:96 and 35:65 relative to the propagation region.

In accordance with still another aspect of the present invention, a disposable garment defines a front waist region, a back waist region, and a crotch region disposed between the front waist region and the back waist region. The garment includes a chassis defining laterally opposing first and second side edges extending along the front waist region, the crotch region, and the back waist region. At least one of the side edges is joined to itself by a seam at the front and back waist regions, respectively, to form a closed side interface defining a leg opening located at a lower end of the side interface, and at least partially defining a waist opening at an upper end of the side interface disposed above the lower end. A tab member extends from the closed side interface, and includes indicia visible to the user. The indicia communicate usage of the tab member to the user.

BRIEF DESCRIPTION OF THE DRAWINGS

Reference is hereby made to the following figures in which like reference numerals correspond to like elements throughout, and in which.

DETAILED DESCRIPTION OF THE INVENTION

Figure 1:
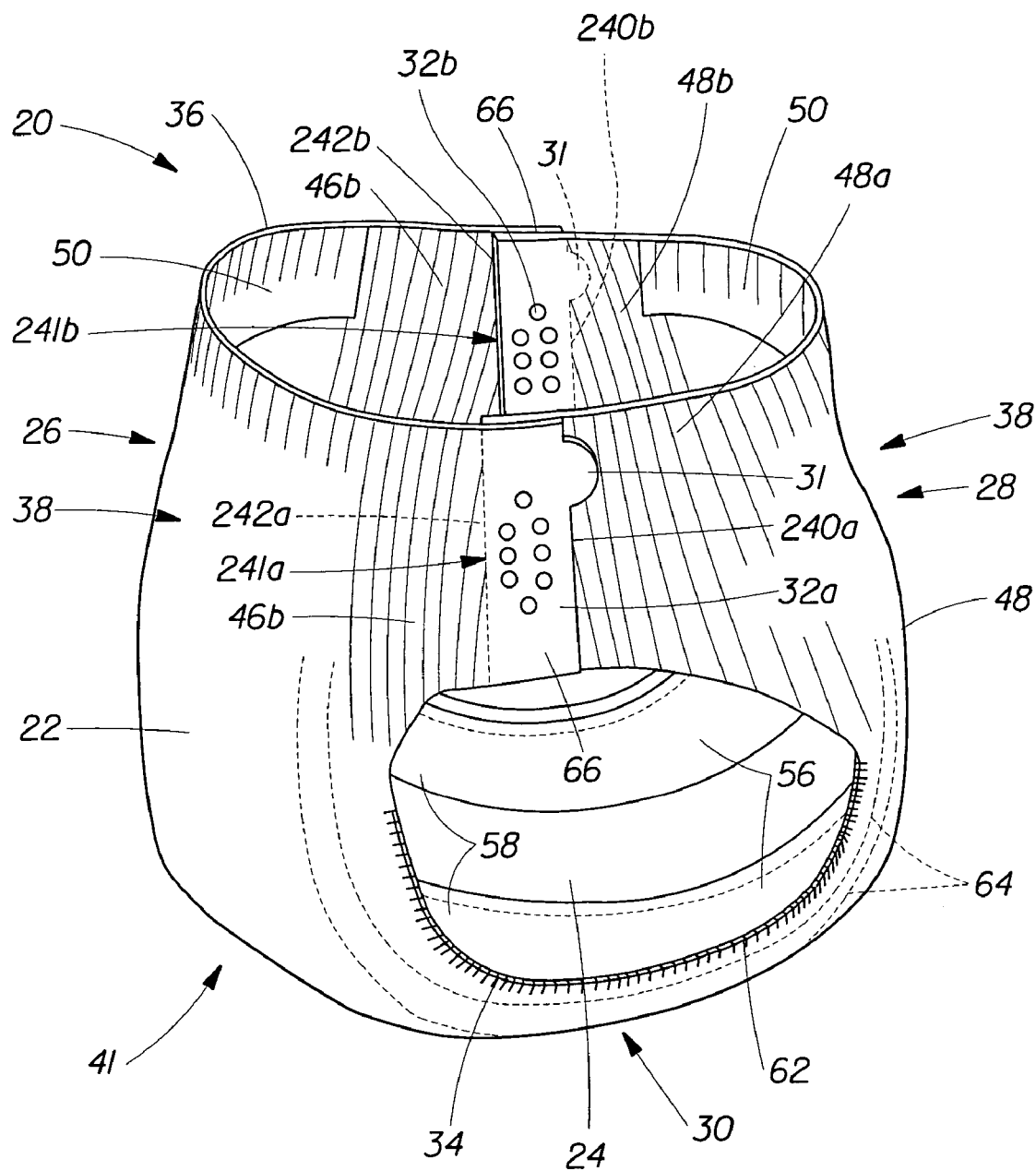
FIG. 1 is a perspective view of a disposable pull-on garment having a pair of adjacent ear panels joined by a side seam constructed in accordance with one embodiment of the invention, whereby the garment is illustrated in a typical in use configuration.

The term "absorbent article" as used herein refers to a device which absorbs and contains body exudates and, more specifically, refers to a device which is placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

The term "diaper" as used herein refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

The terms "pull-on garment" "pull-on diaper" "pant" "training pant" "closed diaper" and "pre-fastened diaper" as used herein refer to disposable garments that have a defined waist opening and a pair of leg openings designed for infant or adult wearers, and that are pulled onto the body of the wearer by inserting the legs into the leg openings and pulling the article up over the waist. A pant may be pre-fastened by any suitable technique including, but not limited to, joining together portions of the article using a seam. A pant may be preformed anywhere along the circumference of the article (e.g., side fastened, front waist fastened, rear waist fastened). The pull-on garment can also be "absorbent" to absorb and contain the various exudates discharged from the body.

The term "seam" as used herein refers to a closure member that joins two portions of an absorbent article, and can be formed from sonic sealed bonds, heat sealed bonds, high pressure bonds, RF bonds, adhesive or cohesive bonds, sewed bonds, autogeneous bonds, bonds fastened via interlocking hooks and loops (i.e., a Velcro® fastener), buttons, and combinations thereof.

The term "user-applied opening force" as used herein refers to a force applied by the user that is intended to open the seam (for instance, when it is desired to remove the garment from the wearer). Examples of a user-applied opening force include tearing forces. The user-applied opening force can include a force applied in a direction from top-to-bottom, a force applied in a direction from bottom-to-top, and a force applied at a middle region of the seam that propagates toward the bottom and top.

A "unitary" pull-on garment as used herein refers to pull-on garments which are formed of separate parts united together to form a coordinated entity.

The term "ear panels" refer to elements that can be formed by at least one layer which also forms the chassis of the garment (i.e., they are not separately manipulative elements secured to the garment, but rather are formed from and are extensions of one or more of the various layers of the diaper). The ear panels can thus define a portion of the chassis. Alternatively, the ear panels can be discrete members that are joined to the chassis.

The term "disposable," as used herein in reference to absorbent articles, means that the absorbent articles are generally not intended to be laundered or otherwise restored or reused as absorbent articles (i.e., they are intended to be discarded after use and, preferably, to be recycled, composted or otherwise discarded in an environmentally compatible manner).

The term "panel" denotes an area or element of the pull-on garment.

The term "joined" or "joining" encompasses configurations whereby an element is directly secured to another by affixing the element directly to the other element, and configurations whereby the element is indirectly secured to the other element by affixing the element to intermediate member(s) which in turn are affixed to the other element.

The term "uncontracted state" is used herein to describe states of pull-on garments in its unseamed, flat and relaxed condition wherein all elastic materials used are removed therefrom.

The terms "body-facing" and "garment-facing" as used herein refer respectively to the relative location of an element or a surface of an element or group of elements. "Body-facing" implies the element or surface is nearer to the wearer during wear. "Garment-facing" implies the element or surface is more remote from the wearer during wear (i.e., element or surface is nearer to the wearer's garments that can be worn over the disposable absorbent article).

The term "disposed" as used herein refers to an element being attached and positioned in a particular place or position in a unitary structure with other elements.

The terms "extendible" and "extensible" as used herein mean that the width or length of the component in the relaxed position can be extended or increased.

The terms "elastic," "elastomer," and "elastomeric" as used herein refer to a material which generally is able to extend to a strain of at least 50% without breaking or rupturing, and is able to recover substantially to its original dimensions after the deforming force has been removed.

Figure 2:
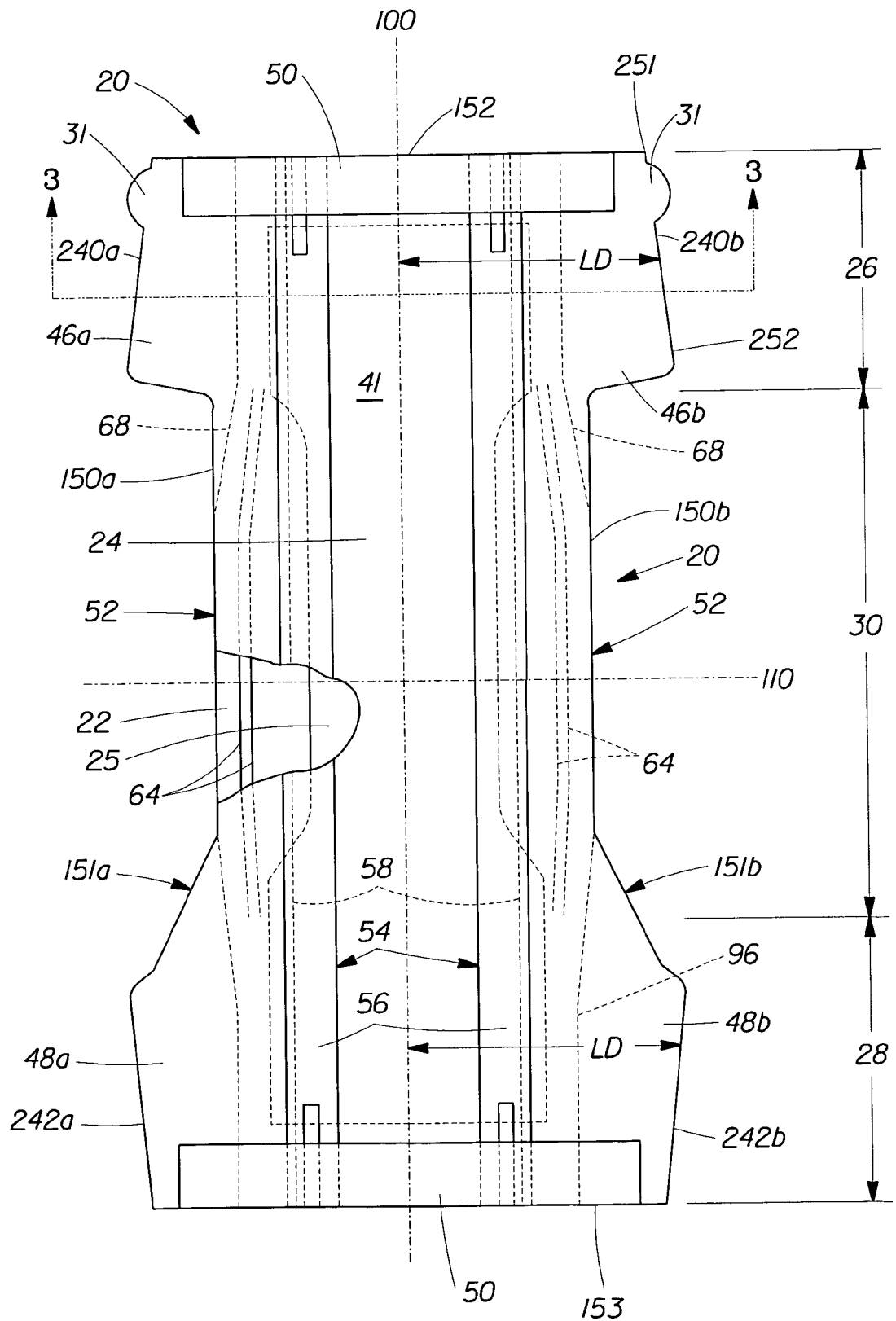
FIG. 2 is a simplified plan view of the disposable pull-on garment illustrated in FIG. 1 shown in its flat uncontracted condition.

Referring to FIGS. 1 and 2, a disposable pull-on garment 20 extends along a longitudinal centerline 100 and a lateral centerline 110. Herein, "longitudinal" refers to a line, axis, or direction in the plane of the pull-on garment 20 that is generally aligned with (e.g. extends substantially parallel to) a vertical plane which bisects a standing wearer into left and right halves when the pull-on garment 20 is worn. Herein, the term "lateral" refers to a line, axis or direction which lies within the plane of the pull-on garment that is generally perpendicular to the longitudinal direction (which divides the wearer into front and back body halves). Directions within 45 degrees of the longitudinal direction are considered to be "longitudinal" and directions within 45 degrees of the lateral direction are considered to be "lateral."

The pull-on garment 20 and component materials thereof also define a body-facing surface which faces the skin of the wearer in use (shown facing the viewer in FIG. 2) and an outer-facing surface facing opposite the body-facing surface (shown facing away from the viewer in FIG. 2), which faces the garment of the wearer if, for instance, the pull-on garment 20 is worn as an undergarment.

The pull-on garment 20 defines a front waist region 26, a back waist region 28, and a crotch region 30 disposed between the front waist region 26 and the back waist region 28. The garment 20 includes a chassis 41 provided in the front waist region 26, the back waist region 28, and in the crotch region 30. The chassis 41 defines longitudinally extending left and right opposing side edges 150a and 150b, respectively that define the laterally outer edges of the garment 20 at the crotch region 30. The chassis 41 further defines laterally extending front and back opposing waist edges 152 and 153, respectively that define the longitudinally outer edges of the garment 20.

The chassis 41 includes a liquid previous topsheet 24, and a liquid impervious backsheet 22 associated with the topsheet 24. An absorbent core 25 can be disposed between the topsheet 24 and the backsheet 22 as illustrated in FIG. 2. The topsheet 24 defines the body-facing surface of the pull-on garment 20 which is positioned adjacent to the wearer's body during use. The backsheet 22 defines the outer-facing surface of the pull-on garment 20 which is positioned away from the wearer's body. The topsheet 24 and the backsheet 22 have length and width dimensions generally larger than those of the absorbent core 25, and extend beyond the edges of the absorbent core 25 to thereby form the side edges 150a-b and the waist edges 152 and 153 of the garment 20.

While the topsheet 24, the backsheet 22, and the absorbent core 25 may be assembled in a variety of well known configurations, exemplary chassis configurations are described generally in U.S. Pat. No. 3,860,003 entitled "Contractible Side Portions for Disposable Diaper" which issued to Kenneth B. Buell on Jan. 14, 1975; and U.S. Pat. No. 5,151,092 entitled "Absorbent Article With Dynamic Elastic Waist Feature Having A Predisposed Resilient Flexural Hinge" which issued to Kenneth B. Buell et al., on Sep. 29, 1992.

The chassis 41 can further include opposing laterally outwardly extending left and right front ear panels 46a and 46b, respectively, disposed at the front waist region 26. The chassis 41 can further include opposing laterally outwardly extending left and right back ear panels 48a and 48b, respectively, disposed at the back waist region 28. The front ear panels 46a and 46b each define opposing left and right side edges 240a and 240b, respectively, that extend between the front waist edge 152 and the corresponding side edges 150a and 150b in the front waist region 26. The back ear panels 48a and 48b each define opposing left and right side edges 242a and 242b in the back waist region 28, respectively, that extend between the back waist edge 153 and the corresponding side edges 150a and 150b. The left and right ear panels 46a and 46b are collectively referred to herein as ear panels 46, and the left and right ear panels 48a and 48b are collectively referred to herein as ear panels 48.

The side edges 240a, 150a, and 242a (including the regions joining the side edge 150a to the side edges 240a and 242a)

cumulatively define one laterally disposed, and longitudinally extending, left side edge 15 of the garment 20. Similarly, the side edges 240b, 150b, and 242b (including the regions joining the side edge 150a to the side edges 240a and 242a) cumulatively define the opposing laterally disposed, and longitudinally extending, right side edge 151b of the garment 20. The garment 20 can define a closed left side interface 241a that is formed by joining the left side edge 151a at the front waist region 26 to the left side edge 151 at the back waist region 28. The garment 20 can further define a closed right side interface 241b by joining the right side edge 151b at the front waist region 26 to the right side edge 151b at the back waist region 28. It should be appreciated that joining only one of the side edges to itself at the front and back waist regions 26 and 28 defines a leg opening 34 and partially defines a waist opening 36, while joining each of the side edges to itself at the front and back waist regions 26 and 28 defines a pant-like garment including a waist opening 36 and a pair of leg openings 34.

At least one of the outermost edges 240 (right edge 240b as illustrated) can have a nonuniform lateral distance LD from the longitudinal center line 100 in the uncontracted state of the garment 20. Likewise, at least one of the outermost edges 242 (right edge 242b as illustrated) can have a nonuniform lateral distance LD from the longitudinal centerline 100 in the uncontracted state of the garment 20. In one aspect of the invention, when the garment 20 is in its uncontracted state, the lateral distance LD from the outer edges 240a-b increases in a direction from the front waist edge 152 toward the lateral centerline 110 (corresponding to a direction extending from the waist opening 36 toward the corresponding leg opening 34 shown in FIG. 1). Furthermore, when the garment 20 is in its uncontracted state, the lateral distance LD from the outer edges 242a-b increases in a direction from the back waist edge 153 toward the lateral centerline 110 (corresponding to a direction extending from the waist opening 36 toward the corresponding leg opening 34 shown in FIG. 1). Alternatively, the lateral distance LD corresponding to either or both of the ear panels side edges 240a-b and 242 a-b can decrease or remain substantially constant in a direction from the corresponding front waist edge toward the lateral centerline 110 when the garment 20 is in its uncontracted state.

In accordance with certain aspects of the present invention, at least one of, or both of, the ear panels 46 and 48 are elastically extensible in at least the lateral direction. In alternative embodiments, the ear panels 46 and 48 are elastically extensible both in the lateral and longitudinal directions. Herein, "extensible" refers to materials that are capable of extending in at least one direction to a certain degree without undue rupture. Herein, "elasticity" and "elastically extensible" refer to extensible materials that have the ability to return to approximately their original dimensions after the force that extended the material is removed. Herein, any material or element described as "extensible" may also be elastically extensible unless otherwise provided. The extensible ear panels 46 and 48 provide a more comfortable and contouring fit by initially conformably fitting the pull-on garment to the wearer and sustaining this fit throughout the time of wear well past when the pull-on garment has been loaded with exudates since the ear panels 46 and/or 48 allow the sides of the pull-on garment to expand and contract.

The ear panels 46 and 48 can be integrally formed with the pull-on garment 20 (i.e., they are not separately manipulative elements secured to the pull-on garment 20, but rather are formed from and are extensions of one or more of the various layers of the pull-on garment 20). In one embodiment, each of the ear panels 46 and 48 is a projected member of the chassis 41. The ear panels 46 and 48 can include at least one unitary element or a continuous sheet material (e.g. the nonwoven outer cover 74 in FIG. 3) that forms a part of the chassis 41 and continuously extends into the ear panels 46 and 48. Alternatively, the ear panels 46 and 48 may be discrete members which do not have any unitary element that forms a part of the chassis 41, and may be formed by joining the discrete members to the corresponding sides of the chassis 41 using any known attachment method.

Figure 4A:
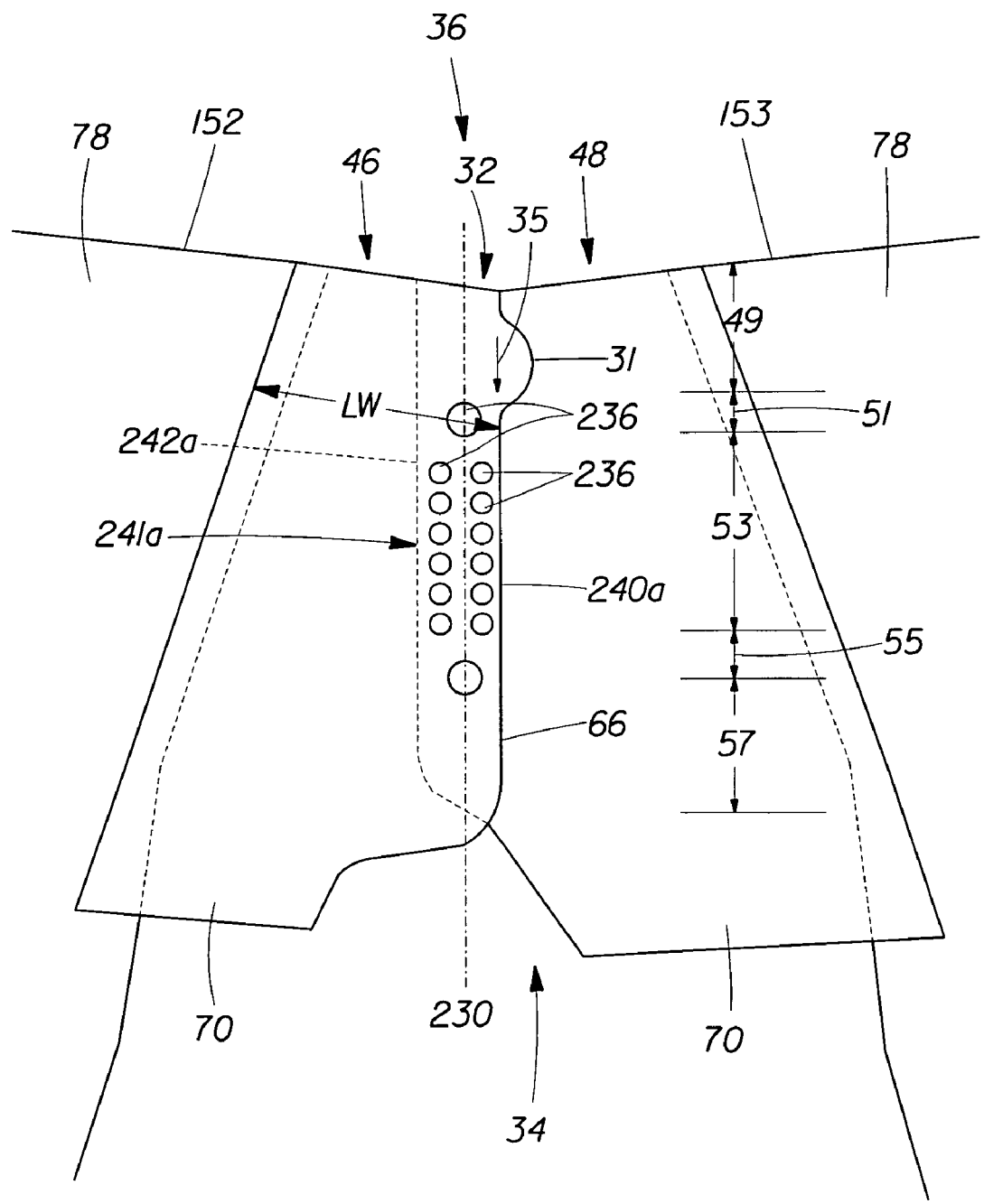
FIG. 4A is an enlarged plan view of a side seam joining the front and back ear panels illustrated in FIG. 1, wherein the side seam includes an initiation region, a leading region, a propagation region, a trailing region, and a completion region.

Referring to FIGS. 1, 2, and 4A, the pull-on garment 20 can further include seam panels 66 extending laterally outward from the ear panels 46 and 48. Each seam panel 66 can be an extension of the corresponding ear panels 46 and 48, or at least one of the component elements used therein. Alternatively, the seam panels 66 can be discrete members attached to, and extending laterally outward from, at least one of the corresponding ear panels 46 and 48. The seam panels 66 thus overlap to define the substantially vertically elongated closed side interfaces 241 that can be seamed to at least partially close the garment and form two encircled leg openings 34 and an encircled waist opening 36 as described above. Each seam panel 66 thus defines a location that can be attached via a first seam 32a that joins the ear panel 46a to the ear panel 48a along the corresponding edges 240a and 240b, and along a second seam 32b that joins the ear panel 46b to the ear panel 48b along the corresponding edges 240b and 242b. In accordance with certain aspects of the present invention, the seams 32a and 32b can be pre-fastened by the manufacturer prior to placing the garment 20 into packaging that is received by the consumer, such that the consumer removes a pre-fastened garment from the packaging.

With continuing reference to FIG. 4A, each seam 32 is formed on a seaming axis 230 which can be determined from any straight lines which may be drawn in the side interface 241a between the edges 240a and 242a. The seaming axis 230 is formed along, and can extend parallel to, the corresponding edges 240 and 242. In accordance with an alternative embodiment, a straight line which equally divides the side interface 241a is chosen as the seaming axis 230 as shown in FIG. 4A. Each seam 32 can be formed from a plurality of discrete seaming bonds 236 which are spaced apart from each other and formed on (or substantially along) the seaming axis 230.

The bonds 236 of the seam 32 can be achieved by any suitable means known in the art appropriate for the specific materials employed in the ear panels 46 and 48. Thus, suitable bond types include discrete bonds such as sonic sealed bonds, heat sealed bonds, high pressure bonds, RF bonds, adhesive or cohesive bonds, sewed bonds, autogeneous bonds, bonds fastened via hooks and loops, buttons, and combinations thereof. In accordance with one aspect of the invention, the seam panels 66 are joined by a predetermined pattern of heat/pressure or ultrasonic welds which withstands the forces and stresses exacted onto the seam 32 during application and wear of the garment 20.

In one aspect of the invention, the seaming axis 230 leans to the longitudinal center line 100 in the uncontracted state of the garment 20. The seaming axis 230 defines a lateral distance between itself and the longitudinal center line 100 that increases in a direction from the waist opening 36 toward the leg opening 34. Alternatively, the seam 32 can be configured such that the lateral distance between the seaming axis 230 and the longitudinal center line 100 decreases in a direction from the waist opening 36 toward the leg opening 34.

The edges 240 and 242 of the ear panels 46 and 48 can define an overlapping configuration or a surface-to-surface configuration. For instance, as illustrated in FIG. 1, longitudinally aligned edges of front and back ear panels 46 and 48 are overlapped and seamed directly or indirectly (e.g., through the side seam panels 66) to define an overlapped (i.e., interior surface-to-exterior surface, or vice versa) configuration. Alternatively, referring to FIG. 7, longitudinally aligned front and back ear panels 46 and 48 are fastened in an interior-to-interior surface configuration. Alternatively still, longitudinally aligned front and back ear panels 46 and 48 can be fastened in an exterior-to-exterior surface configuration. Interior-to-interior and exterior-to-exterior surface configurations are also referred to herein as "butt seams".

Because the panels 46 and 48 are extensible, substantial forces can be generated across the seam 32 during use as the garment 20 is worn. For instance, if the seam 32 defines an overlapped configuration as illustrated in FIG. 1, the seam 32 is likely to experience substantial shear forces during application and use of the garment 20 that tend to separate the side edges 240 and 242. Alternatively, if the seam 32 defines a surface-to-surface configuration as illustrated in FIG. 4A, the seam 32 is likely to experience substantial tensile forces during application and use of the garment 20 that tend to separate the side edges 240 and 242. Whether the seam 32 is an overlapped seam or a butt seam, the forces imparted onto the seam 32 during use are exacerbated in response to wearer movement. Accordingly, the bonds 236 at the seam 32 are sufficiently strong to maintain their integrity during normal use, and are arranged having bond characteristics that provide a reliably breakable bond when the user wishes to remove the garment 20 from the wearer.

Accordingly, in order to ensure that the seam 32 is sufficiently strong to withstand the forces experienced during use, while at the same time providing for predictable and reliable opening in response to a user-applied opening force, the seam 32 can be divided into a plurality of regions. Specifically, as illustrated in FIG. 4A, the seam can define an initiation region 49, a leading region 51, a propagation region 53, a trailing region 55, and a completion region 57. The initiation region 49 extends down from a location proximal the waist opening 36, and the leading region 51 extends down from the initiation region 49 towards the corresponding leg opening 34. The propagation region 53 extends down from the leading region 51 toward the leg opening 34, and terminates short of the leg opening 34. The trailing region 55 extends down from the propagation region 53 toward the leg opening, and terminates short of the leg opening. The completion region 57 extends down from the trailing region 55, and can terminate at the leg opening 34.

Each of the regions 49, 51, 53, 55, and 57 can differ from each other in terms of bond type, bond strength, the bond density (i.e., number of bonds per unit area in a given region), the geometric configuration (e.g., shape of the bonds 236 including circles, ovals, triangles, squares, rectangles, and other polygons), length, width, and orientation of individual bonds, and the spatial arrangement of the bonds 236. The regions 49, 51, 53, 55, and 57 can furthermore be intermittently or continuously bonded (for instance, with respect to the vertical direction). Accordingly, it can be said that the regions 49, 51, 53, 55, and 57 can have non-homogeneous bond characteristics. Furthermore, the bonds within each of the regions 49, 51, 53, 55, and 57 can define non-homogenous bond characteristics. It should be further appreciated that certain bond characteristics may be homogeneous across two or more of the regions 49, 51, 53, 55, and 57, each of which will now be described.

In particular, with continuing reference to FIG. 4A, the initiation region 49 is intended to produce an unbonded length of material between the waist opening 36 and the leading region 51 at the closed side interface 241 that is sufficiently sized to provide the user with leverage when opening the seam 32. As illustrated, the upper end of the initiation region 49 terminates at the waist opening 36, and the lower end of the initiation region terminates at the leading region 51. In accordance with one aspect of the invention, the ratio of the length of the initiation region 49 (vertical length when the garment 20 is configured as a pant shown in FIG. 4A) to the length of the propagation region 53 is between about 4:96 and 35:65, and alternatively between 4:96 and 20:80. In accordance with another aspect of the invention, the length ratio of the initiation region 49 to the remainder of the seam 32 is between about 4:96 and 35:65, and alternatively between about 4:96 and 20:80.

The present invention recognizes that longer initiation regions will provide the user with increased leverage when opening the seam 32. As a result of the leverage provided by the initiation region 49, the user-applied opening force is magnified at the bonds 236 that are being opened below the initiation region 49. However, longer initiation regions decrease the available bond area at the seam 32. One embodiment of the present invention, therefore, is to provide a seam 32 having an initiation region 49 that provides the requisite leverage while, at the same time, providing a seam that will withstand the forces experienced during use. In accordance with certain aspects of the present invention, the initiation region 49 extends down from the waist opening 36 a distance that is within a range having a lower end defined by and between about 4 mm and 15 mm (i.e., including 5, 6, 7, 8, 9, 10, 11, 12, 13, and 14 mm) and having an upper end defined by and between about 15 mm, 30 mm, 40 mm, and 50 mm. In accordance with another aspect of the present invention, the initiation region 49 can extend down from the waist opening 36 a distance that is up to 30% the length of the closed side interface 241 and, alternatively, up to 30% of the length of the seam 32.

The initiation region 49 can be completely unbonded (i.e., unseamed) to provide the gap between the waist opening 36 and the leading region 51 as illustrated in FIG. 4A. As used throughout this description, the term "unbonded" refers to portions which are not joined to other materials. While the initiation region 49 is positioned at the upper end of the closed side interface 241 as illustrated, one having ordinary skill in the art will appreciate that the initiation region 49 could alternatively be disposed at the lower end of the closed side interface 241. Accordingly, the initiation region 49 can thus be said to provide a "gap" that includes the minimum vertical distance between an upper or lower edge of the article 20 (i.e., the waist opening 36 or leg opening 34) and one of the elements of the seam 32 that provides increased leverage to the user when applying the opening force to the seam 32.

Figure 4B:
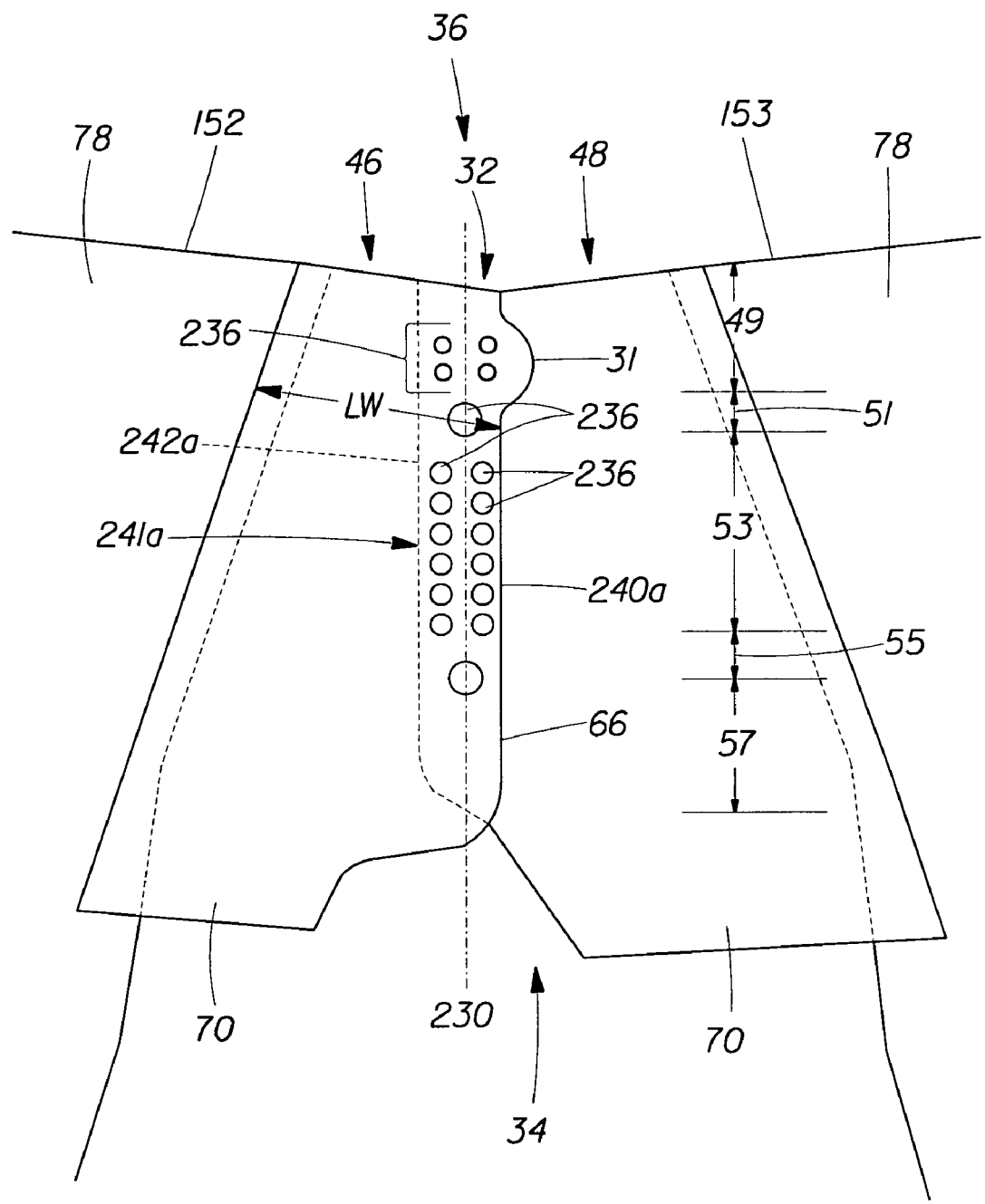
FIG. 4B is an enlarged plan view of a side seam joining the front and back ear panels similar to FIG. 4A, but with the initiation region constructed in accordance with an alternative embodiment.
Figure 4C:
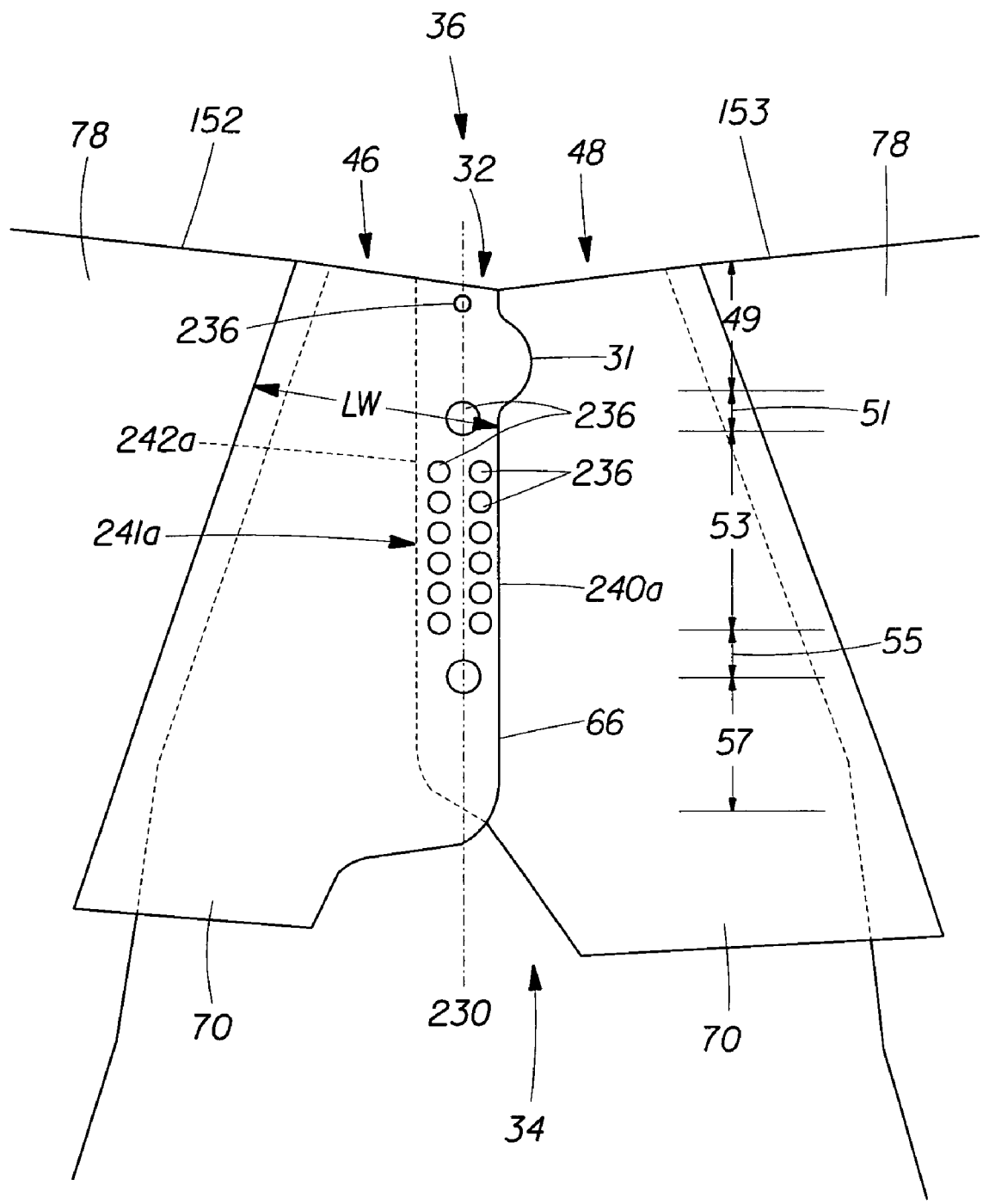
FIG. 4C is an enlarged plan view of a side seam joining the front and back ear panels similar to FIG. 4A, but with the initiation region constructed in accordance with an alternative embodiment.

Alternatively, as illustrated in FIG. 4B, the initiation region 49 can include one or more stabilizing bonds 236 that tack the ear panels 46 and 48 together to prevent the ear panels from flapping unpredictably during use, and to further prevent unintentional opening of the seam 32. As illustrated in FIG. 4C, the one or more bonds 236 of the propagation region 49 can be disposed adjacent the upper end of the closed side interface 241*a* (i.e., adjacent the upper edge 152 and/or the upper edge 153, and also adjacent the waist opening 36). If the initiation region is bonded, the bonds 236 therein have a relatively low or nominal bond strength, and do not provide a substantial resistance to the user-applied opening force, and further can be incapable of withstanding substantial shear forces during garment application and use. Without being bound by theory, the present inventors believe that the bond strength of the region adjacent the initiation region 49 can be sufficiently strong to absorb the in-use forces and prevent unintentional opening of the initiation region 49 during use.

Whether the initiation region 49 is bonded, unbonded, or a combination of both, the initiation region 49 can be said to possess a bond strength (i.e., provides a resistance to the user-applied opening force) that is less than the resistance of the leading region 51, the propagation region 53, and the trailing region 55, and potentially the completion region 57. The present invention recognizes that bonds 236 in the initiation region 49 may fail during use. However, such failure does not run contrary to the teachings of the present invention as the initiation region 49 is intended to include unattached, or easily unattachable, side seam portions that provide the user with leverage when opening the seam 32. The side seam 32 is configured to maintain its intended bond integrity even if bonds 236 in the initiation region 49 fail during use.

Referring again to FIG. 4A, the leading region 51 exhibits a strength that is sufficient to prevent the seam 32 from opening in response to forces experienced during normal use and, furthermore provides a substantially increased resistance to the user-applied opening force. The high bond strength at the leading region 51 is configured to withstand high shear and/or tensile forces experienced during application of the garment 20 onto the wearer or during use, and thereby prevent unintended opening of the seam 32. As described above, however, the leverage provided by the separated ear panels 46 and 48 at the initiation region 49 advantageously magnifies the user-applied opening force and enables the user to easily open the leading region 51.

As illustrated in FIG. 4A, the leading region 51 can include one bond 236 having a substantially greater bond strength (i.e., resistance to the user-applied opening force) than the other bonds 236 that may be present in the initiation region 49, the propagation region 53 or, for that matter, the entire seam 32. Alternatively, the leading region 51 can comprise a cluster of bonds 236 that can be spatially arranged in any desired configuration. The present inventors recognize that a cluster of bonds 236 in close proximity may cumulatively require a user-applied opening force greater than that to open each of the individual bonds that forms the cluster. For instance, referring to FIG. 4D, the leading region 51 can comprise a pair of vertically aligned bonds 236 as illustrated. Alternatively, referring to FIG. 4E, the leading region 51 can comprise a pair of horizontally aligned bonds 236 as illustrated. Alternatively still, referring to FIG. 4F, the leading region 51 can comprise a two pair of vertically and horizontally aligned bonds 236 as illustrated. One having ordinary skill in the art will readily appreciate that FIGS. 4A and 4D-4F are merely representative of exemplary leading region configurations, and that the number bonds 236 can be greater than that illustrated, and that the orientation of bonds 236 could also differ so long as the leading region provides resistance to the user-applied opening force as described above.

It will thus be appreciated that the leading region 51 provides an area of reinforcement that prevents undesired failure during application and wear of the garment 20.

The propagation region 53 contains a plurality of bonds 236 that are sufficiently strong to resist forces during use, especially when used in combination with the leading region 51. Without being bound by theory, it is believed that the bond strength of the leading region 51 absorbs a substantial portion of the forces experienced during application and use, such that the bond strength of the propagation region 53 can be less than that of the leading region 51 (but higher than the bond strength of the initiation region 49). The propagation region 53 provides a resistance to the user-applied opening force that is less than that of the leading region 51 but greater than that of the initiation region 49. Because the leading region 51 is stronger than the propagation region 53, the user-applied opening force that opens the bonds 236 at the leading region 51 can also open the bonds 236 at the propagation region 53 in sequence as one continuous motion.

The bonds 236 in the propagation region 53 can be arranged as a pair of adjacent bond columns that are aligned (and extend substantially vertical as illustrated in FIG. 4A) to assist in the propagation of bond opening as the user continues to apply the opening force to the seam 32. Alternatively, as illustrated in FIG. 4G, the bonds 236 in the propagation region 53 can be staggered or, as illustrated in FIG. 4H, the bonds 236 in the propagation region 53 can form a single bond column extending along, or parallel to, the seaming axis 230. The bonds 236 can further be arranged in more than two columns. One skilled in the art will appreciate that the bonds 236 in the propagation region 53 can be spatially arranged in any regular or irregular configuration suitable to facilitate opening of the bonds 236 at the desired forces.

Figure 4D:
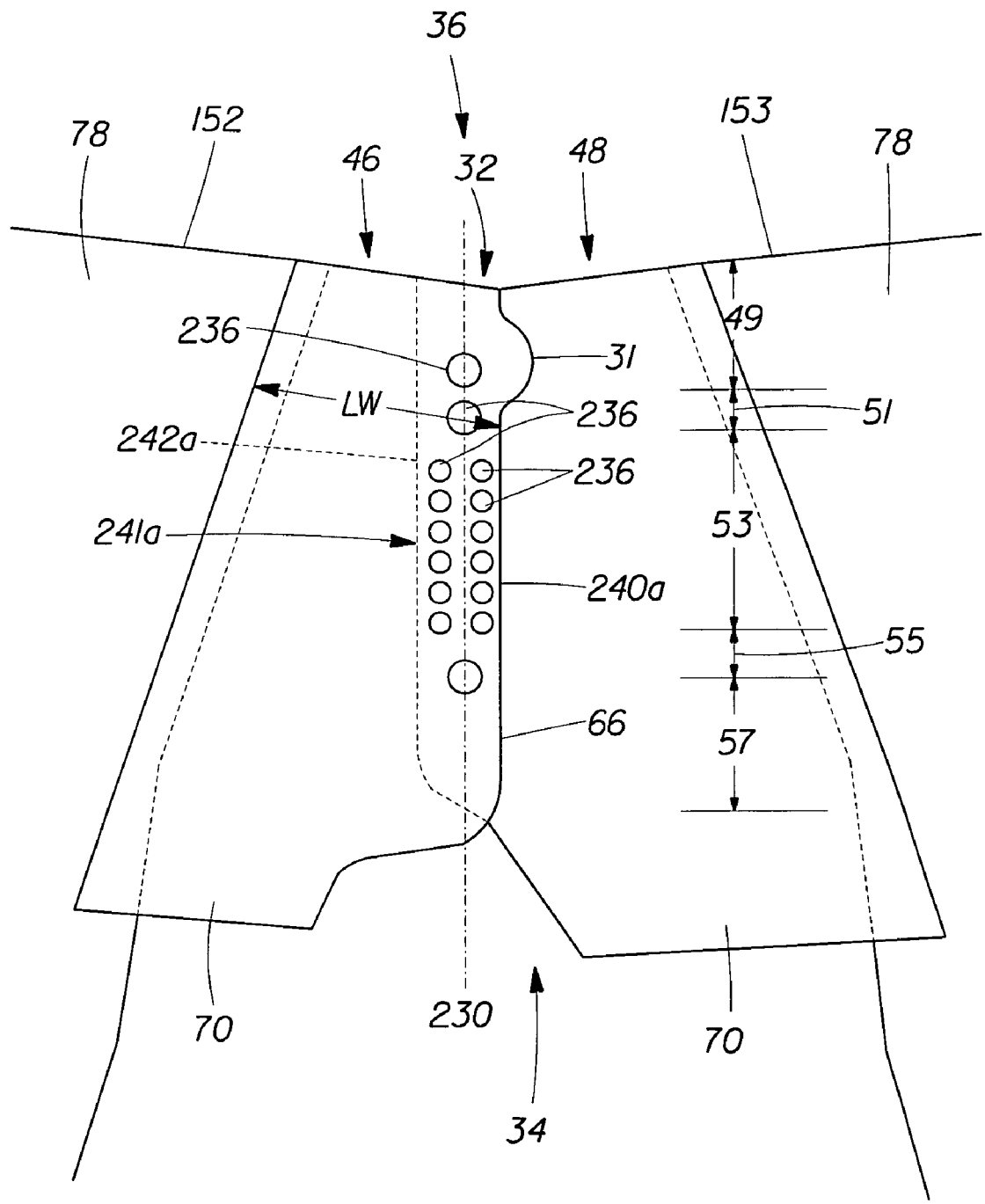
FIG. 4D is an enlarged plan view of a side seam joining the front and back ear panels similar to FIG. 4A, but with the leading region defining a cluster of bonds in accordance with an alternative embodiment.
Figure 4E:
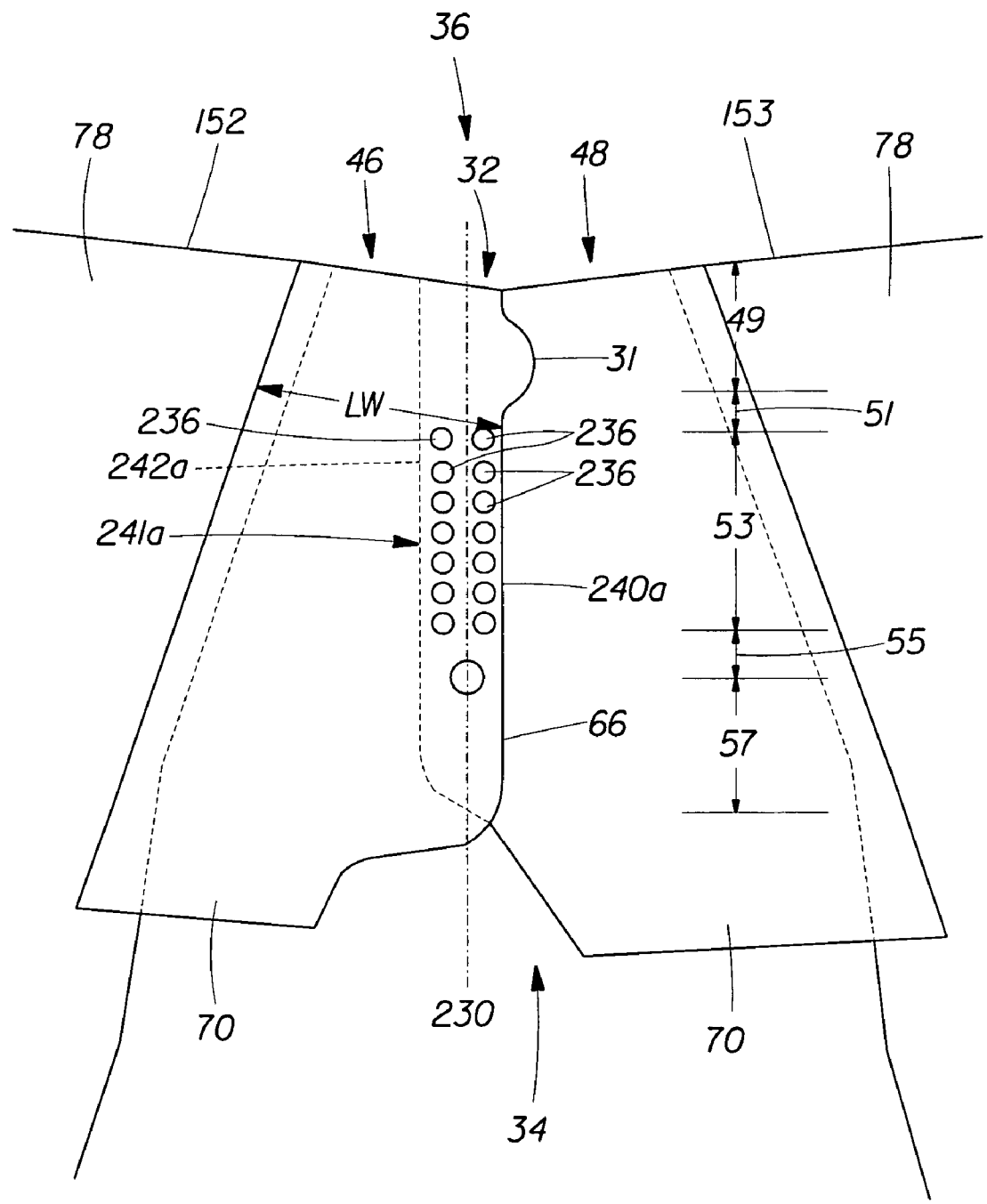
FIG. 4E is an enlarged plan view of a side seam joining the front and back ear panels similar to FIG. 4A, but with the leading region defining a cluster of bonds constructed in accordance with an alternative embodiment.
Figure 4F:
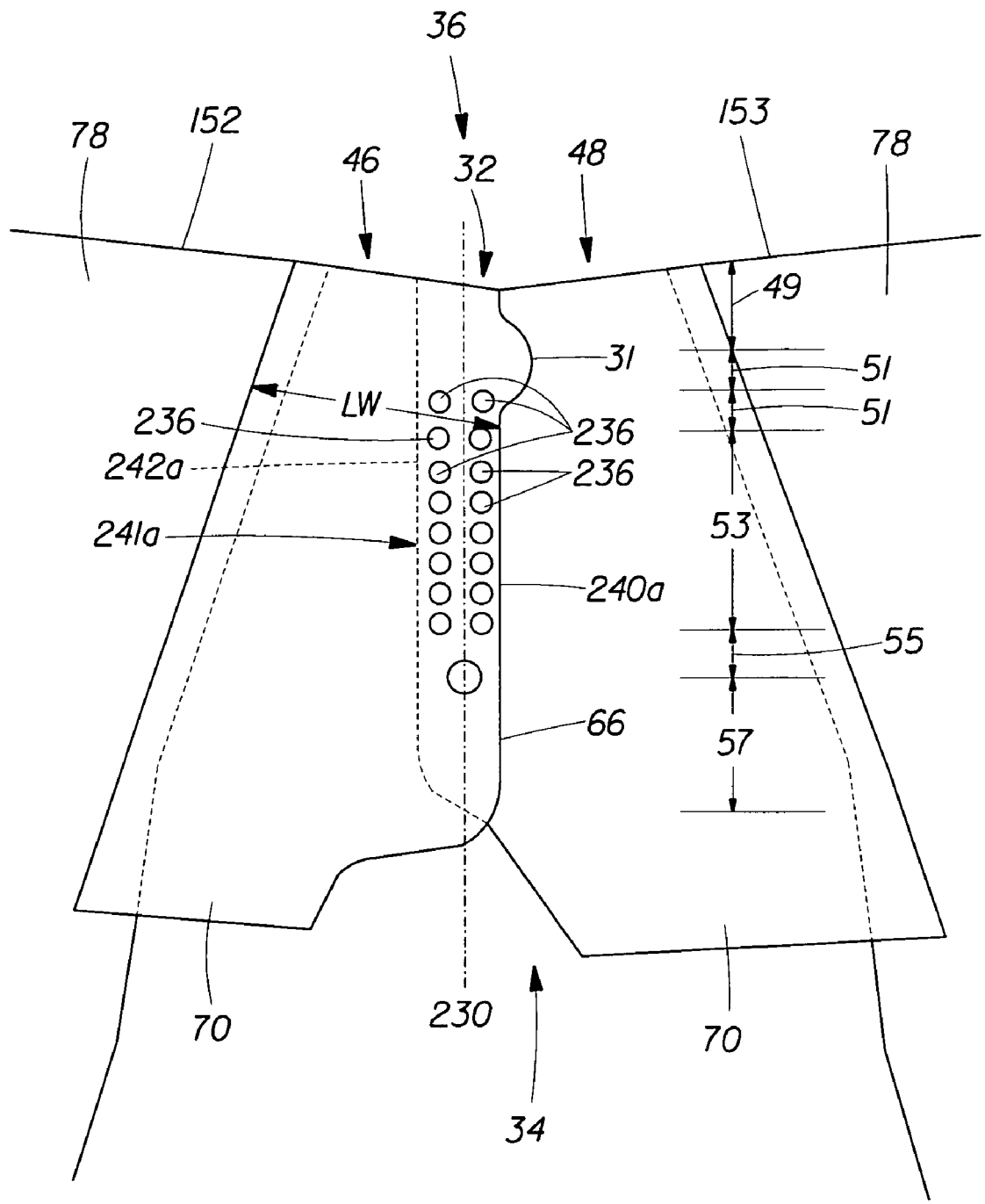
FIG. 4F is an enlarged plan view of a side seam joining the front and back ear panels similar to FIG. 4A, but with the leading region defining a cluster of bonds constructed in accordance with an alternative embodiment.
Figure 4G:
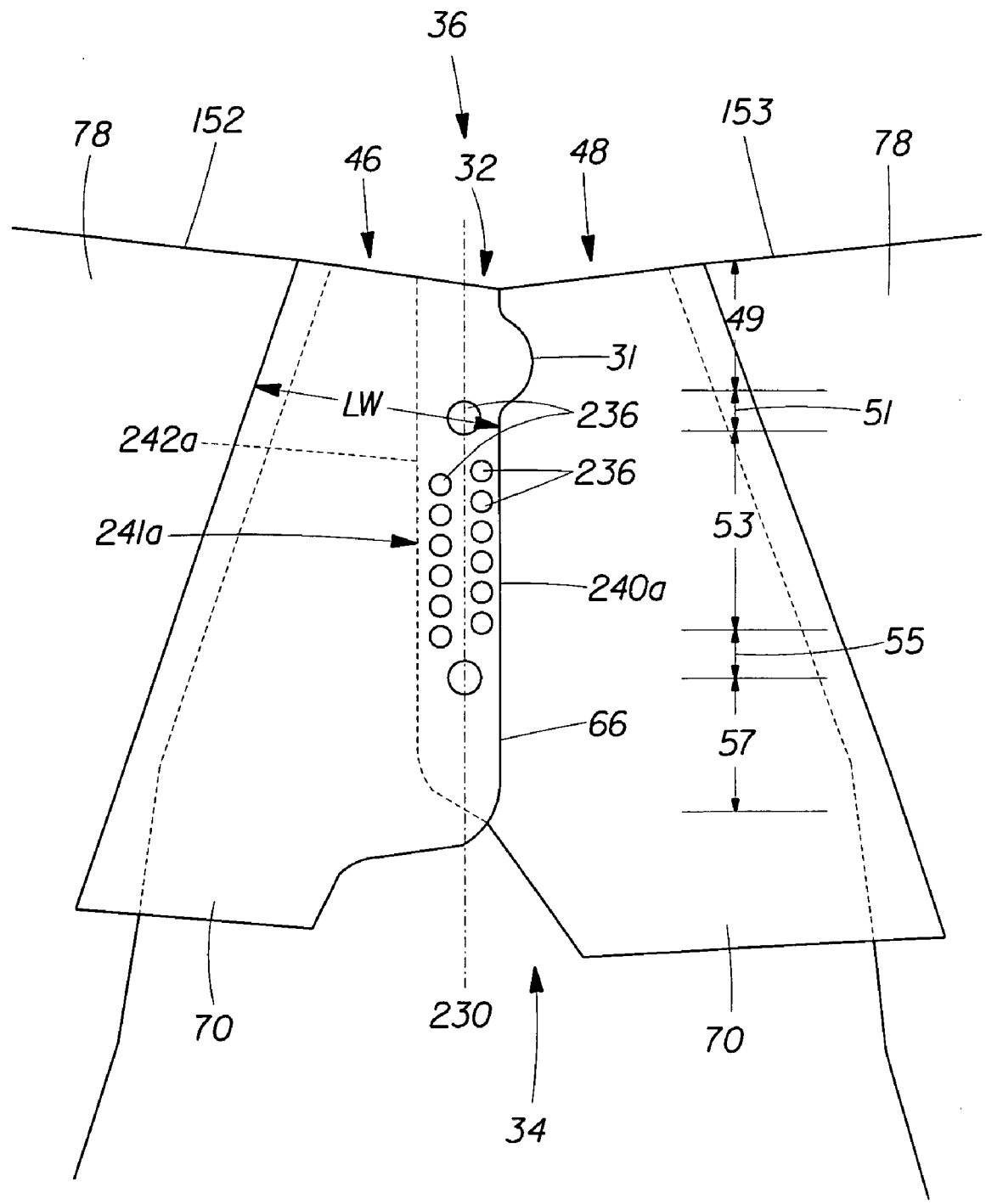
FIG. 4G is an enlarged plan view of a side seam joining the front and back ear panels similar to FIG. 4A, but with the propagation region constructed in accordance with an alternative embodiment.
Figure 4H:
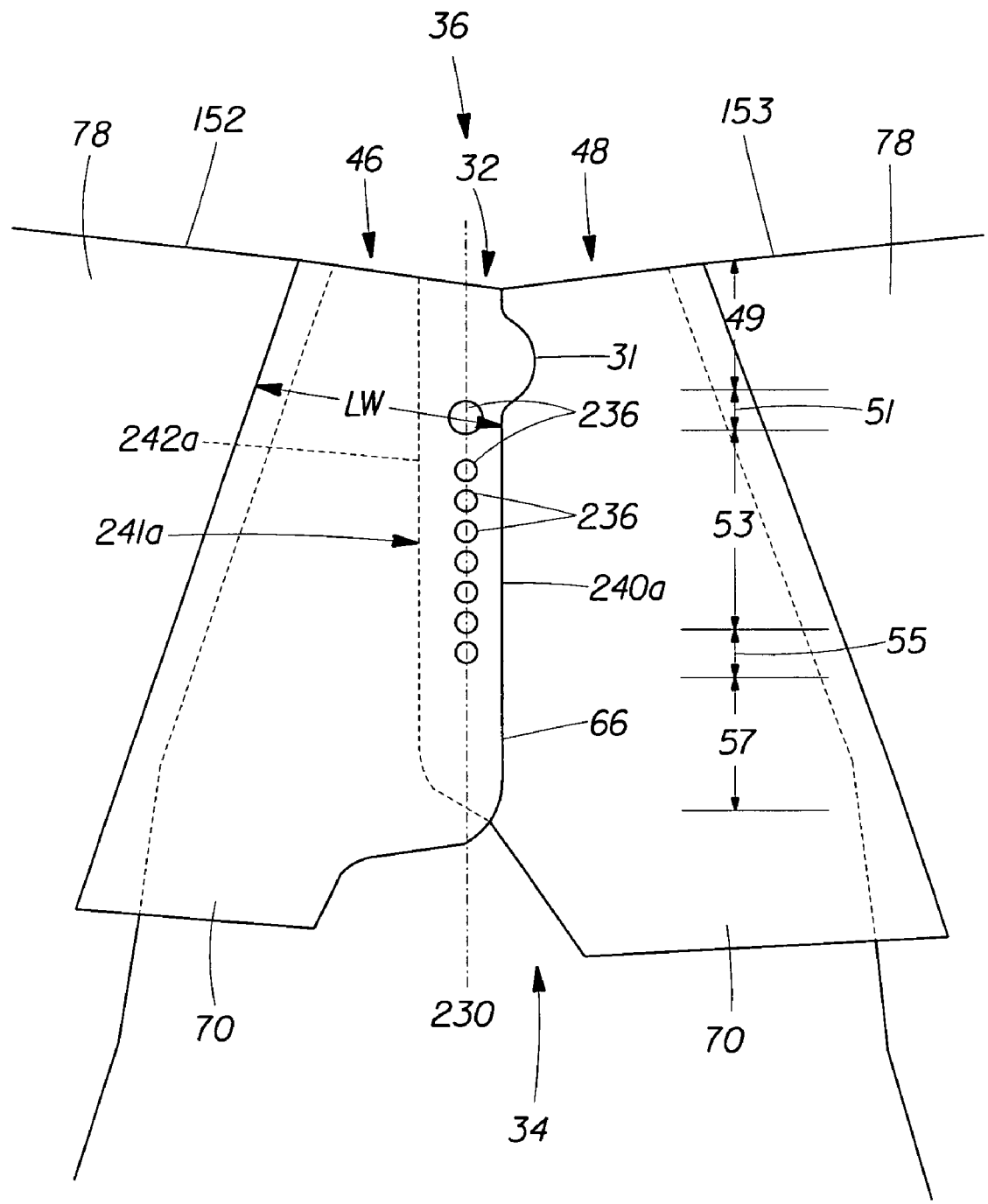
FIG. 4H is an enlarged plan view of a side seam joining the front and back ear panels similar to FIG. 4G, but with the propagation region constructed in accordance with another alternative embodiment.
Figure 4I:
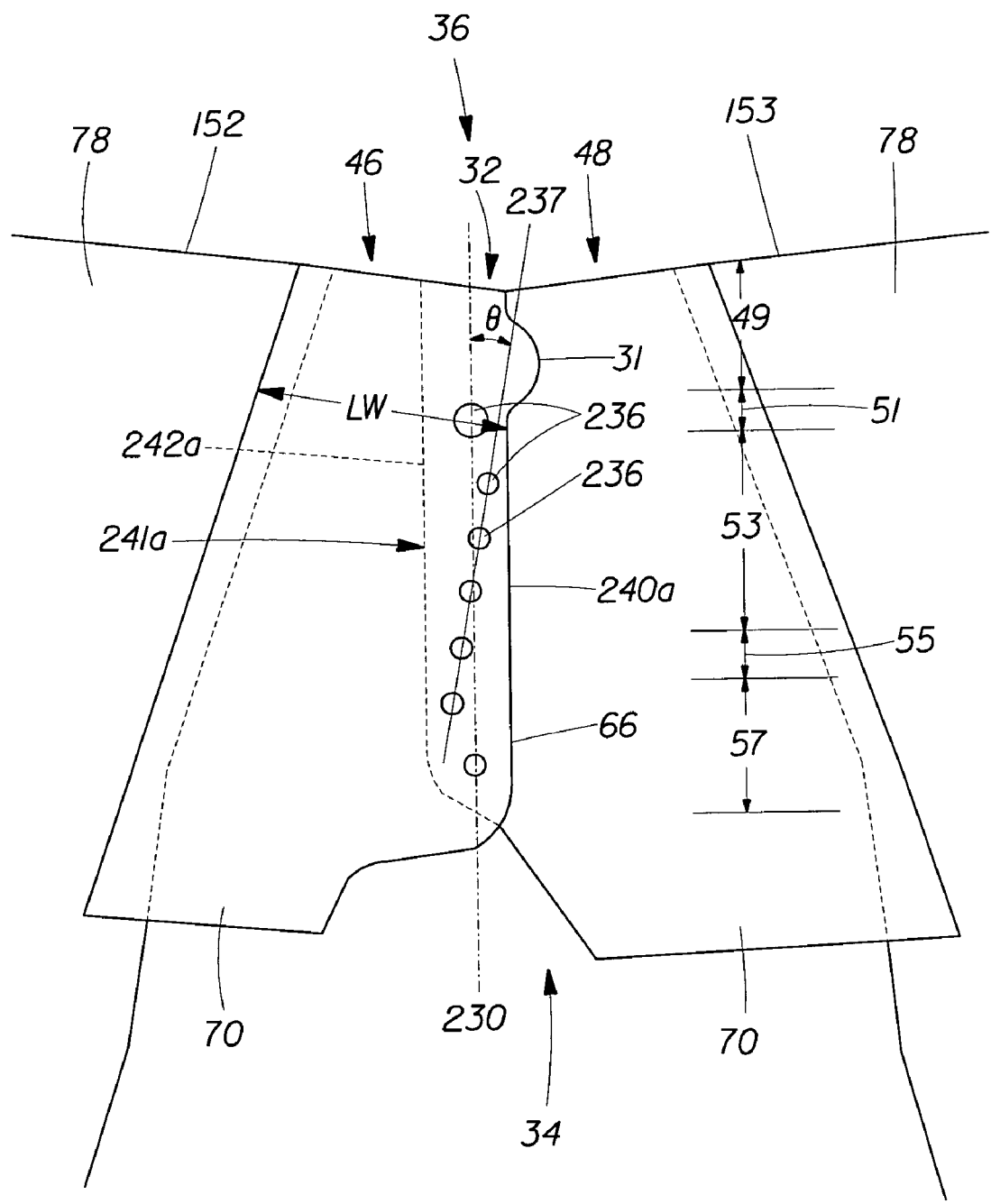
FIG. 4I is an enlarged plan view of a side seam joining the front and back ear panels similar to FIG. 4G, but with the propagation region constructed in accordance with still another alternative embodiment.
Figure 4J:
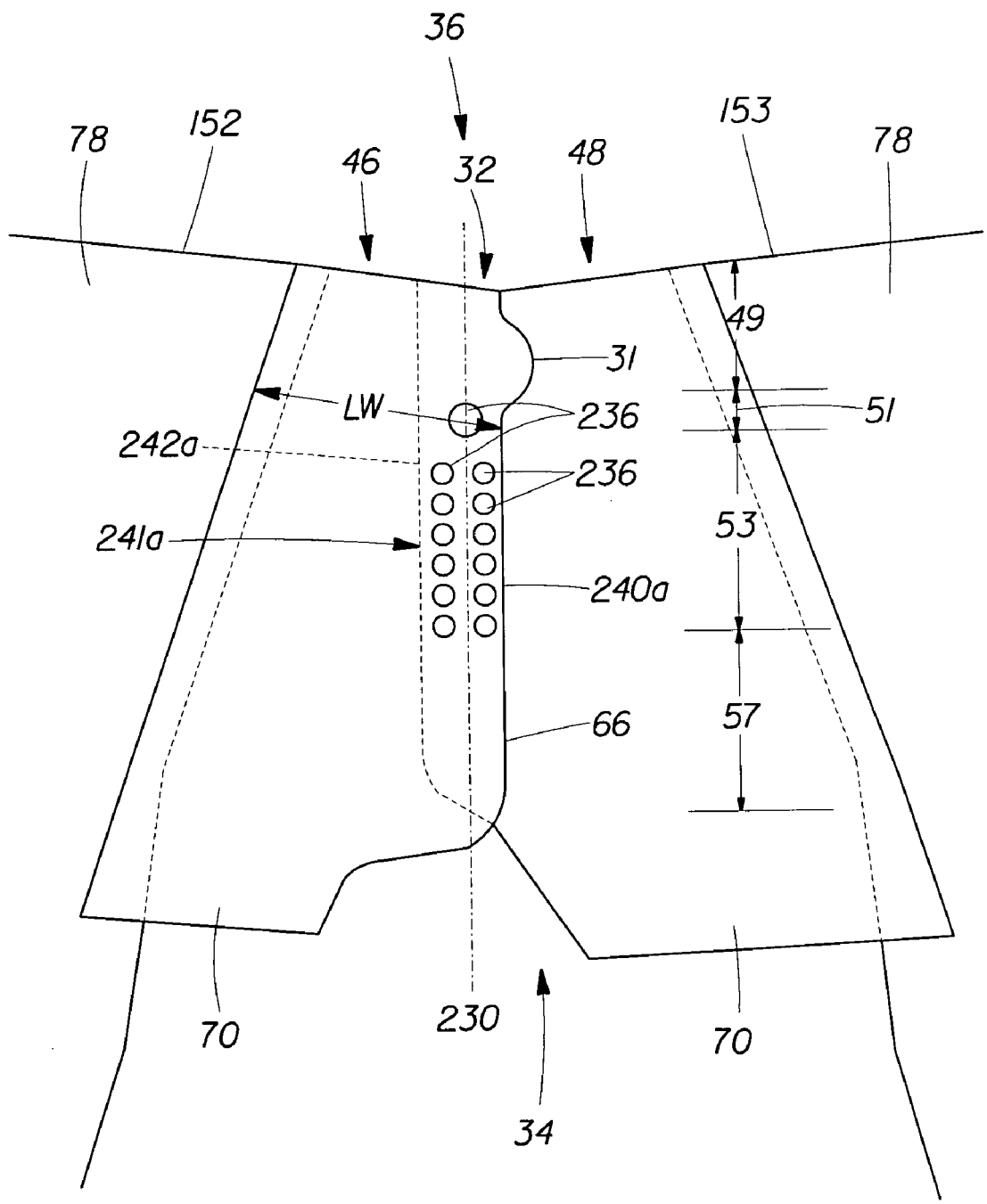
FIG. 4J is an enlarged plan view of a side seam joining the front and back ear panels similar to FIG. 4A, wherein the side seam is constructed in accordance with another alternative embodiment.

For instance, in accordance with another alternative embodiment illustrated in FIG. 4I, the bonds 236 in the propagation region 53 (and in fact in any of the regions) can extend along an axis of elongation 237 that provides enhanced resistance to shear forces experienced during use and during application of the garment 20, and to further provide reduced resistance to the user-applied opening force which extends substantially parallel to the direction of extension of the bonds 236 (i.e., substantially vertically) while providing reliable and predictable opening in response to the user-applied opening force. The axis 237 can extend vertically, or the axis can define an angle θ that increases relative to the vertical in a direction from the waist opening 36 towards the leg opening 34, it being appreciated that the user-applied opening force can also increase in this manner if, for instance, the user opens the garment 20 in one continuous motion.

It should be appreciated that the bond strength of the initiation region 49 can increase in a direction from the waist opening 36 towards the leg opening 34, as the greater bond strengths provide additional resistance to the sear and tensile forces experienced during use while, at the same time. However, the greater bond strengths may not be felt by the user who is opening the seam 32 open because the leverage afforded to the user increases as the seam 32 is continuously opened.

As illustrated in FIG. 4A, the trailing region 55 can be disposed between the propagation region 53 and the completion region 57, and can include one or more bonds 236 that have a bond strength (i.e., resistance to the user-applied opening force) that is slightly higher than that of the propagation region 53. The present inventors anticipate that the peak forces experienced proximal the waist opening 36 are greater than the peak forces experienced proximal the leg openings 34 and, as a result, the bond strength of the trailing region 55 can be less than that of the leading region 51. Alternatively, one skilled in the art will recognize that the trailing region 55 can provide a resistance to the user-applied opening force that is substantially equal to or greater than that of the leading region 51, it being appreciated that bond strengths can increase in a direction from the waist opening 36 towards the leg opening 34 as described above.

The completion region 57 can be configured to easily allow the user to complete the separation of the ear panels 46 and 48 in the same motion. The completion region 57 can thus be constructed symmetrical to the initiation region 49 described above, and is configured to open easily in response to the user-applied opening force that is applied through the propagation region 53 and trailing region 55.

Figure 4K:
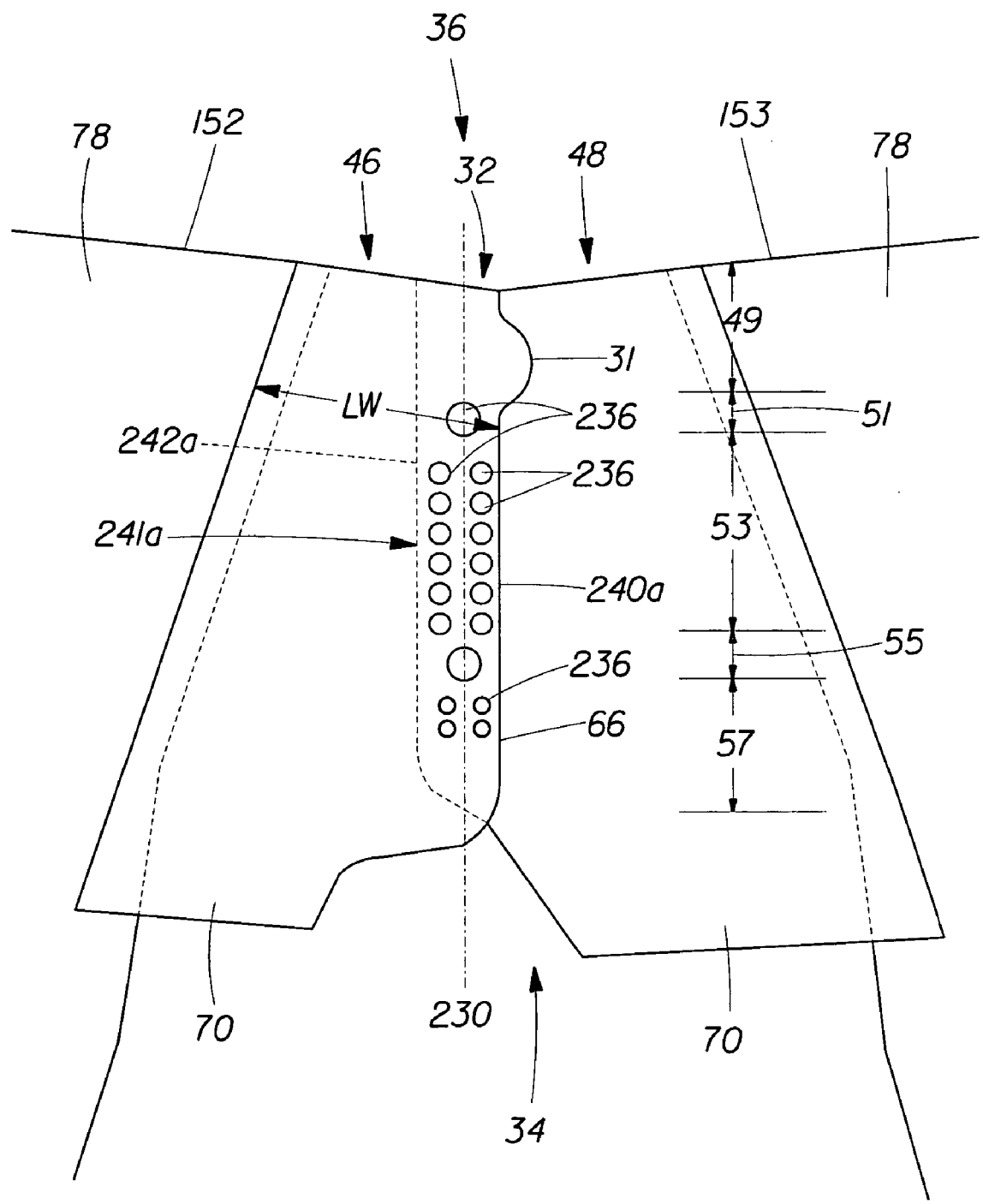
FIG. 4K is an enlarged plan view of a side seam joining the front and back ear panels similar to FIG. 4A, but with the completion region constructed in accordance with an alternative embodiment.

Specifically, the completion region 57 can be completely unbonded as illustrated in FIG. 4A, or include one or more bonds 236 (See FIG. 4K) that provide the completion region 57 with a bond strength constructed to be substantially similar or identical to that required at the initiation region 49. The present invention recognizes that, if the user applies a continuous opening force down the entire side seam 32, the force will be applied in a direction that becomes increasingly angularly offset from the vertical. If the bonds 236 of the completion region 57 are too strong, the likelihood would increase that the force would cause the panel 66 to tear or fail instead of the bonds 236. Because at least a portion of the completion region 57 extending from the corresponding leg opening 34 can be unbonded, instances of red marking the skin of the wearer, and wearer discomfort generally, can be reduced by the present invention, as described in U.S. Patent Publication No. 2003/0120240 A1 (published Jun. 26, 2003 to Buell, et al). Furthermore, because at least a portion of the completion region 57 is unbonded, the completion region 57 can be grabbed by a user to commence application of the user-applied opening force.

It should be appreciated that while the seam 32 defines the five regions 49, 51, 53, 55, and 57 in accordance with certain aspects of the present invention, the seam 32 could omit one or more of the regions without departing from the scope of the present invention, unless otherwise specified. Alternatively, the seam 32 could include more than the five regions described without departing from the scope of the present invention, unless otherwise specified. Alternatively still, certain regions may be disposed in different relative positions as will be described in more detail below with reference to FIGS. 8A and 8B. Accordingly, unless otherwise specified, the present invention is not intended to be limited to the relative position and configurations of the regions 49, 51, 53, 55, and 57 of the embodiments illustrated and described above.

Furthermore, the regions 49, 51, 53, 55, and 57 may not comprise individual bonds 236 as illustrated, but instead can comprise a conventional hook-and-loop type fasteners. Accordingly, the term "bonded" as used herein in the context of two elements refers to any fastener (be it discrete bonds or a continuous mechanical fastener) that connects the two elements together.

While each of the regions 49, 51, 53, 55, and 57 is configured to open its corresponding bond(s) 236 in response to the user-applied opening force, the present invention recognizes that, at times, portions of the garment 20 surrounding the side seam 32 may at times tear or fail instead while opening the seam 32. However, such tearing or failure is reduced with respect to the prior art, and is located closer to the side seam 32 than in conventional absorbent articles. Accordingly, even if portions of the garment 20 surrounding the side seam 32 tear or fail, it is possible that, as the opening force continues, the tearing and failure of the surrounding garment 20 will cease and the ear panels 46 and 48 will continue to open as the bonds 236 are once again separated.

While exemplary bond patterns and characteristics have been illustrated and described above, the present invention is intended to include any bond pattern or configuration capable of withstanding the shear forces experienced during use and reliably and predictably failing upon the user-applied opening force, as appreciated by one having ordinary skill in the art.

Referring again to FIG. 4A, the garment 20 can include at least one tear-open tab 31 extending from at least one of the seam panels 66 (and hence one or both of the ear panels 46 and 48) that comprise a given seam 32. The tab 31 can be an extension of the corresponding seam panel 66 or at least one of its component elements used therein. Alternatively, the tear-open tab 31 can be a discrete member that is attached to the seam panels 66 as desired. The tab 31 can extend outward from the seam a distance of at least about 5-15 mm, including increments of 1 mm therebetween, and can be disposed proximal the upper end of the side interface 241a. The tab 31 has an upper edge that extends outwardly from the seam panel 66 that can be aligned with the upper edge 152 or 153, or can be disposed slightly below the waist opening 36 as illustrated in FIG. 4A. In accordance with certain aspects of the invention, the upper edge is disposed within a range between and including about 0 mm and 10 mm (including 1, 2, 3, 4, 5, 6, 7, 8, and 9 mm) below the waist opening 36. Advantageously, the upper edge of the tab 31 is disposed above the leading region 51 (if present) to increase the leverage provided to the user when opening the seam 32. The tab 31 further defines a lower edge that extends out from the seam panel 66 that define virtually any distance down from the upper edge. The lower edge can be disposed above the leg opening 34, or can extend down to the leg opening 34.

Accordingly, the tab 31 can be partially aligned laterally with the initiation region 49 as shown in FIG. 4A or partially aligned with the initiation region 49 and the leading region 51 as shown in FIG. 4D. It should be appreciated, however, that the tab 31 could alternatively be positioned and arranged in any alternative manner that facilitates intentional opening at the seams 32 after soiling of the pull-on garment 20. For instance, the tab 31 can extend substantially along the entire length of the seam 32 or closed side interface 241. The tab 31 is configured to be grasped by the user when applying the opening force to the side seam 32 to remove the garment 20 from the wearer, and advantageously provides a greater distance (and therefore greater to moment arm) between the user's fingers and the bonds 236 that are being opened. In this regard, it should be appreciated that the initiation region 49 can include, or be solely defined by, the tab 31 if, for instance, the propagation region 53 or leading region 51 extends substantially to the waist opening 36.

With continuing reference to FIG. 4A, the tear-open tab 31 is free from the corresponding underlying ear panel 48, and is thus easily visible to the user. Alternatively, the tab 31 can be fastened to the corresponding underlying ear panels 46 and 48, either via a peelable adhesive or cohesive, or by any suitable mechanical fastening element, such as hooks and loops, or it can be lightly tack bonded such that the tab 31 is easily separable from the underlying ear panel 48. The tab 31 can further be provided with any suitable indicia 35 that can be printed on the exposed surface of the tab 31 (i.e., the surface that is disposed opposite the surface that faces the garment components). Alternatively, the indicia 35 can be disposed on an auxiliary layer that is affixed to the tab 31. Accordingly, the indicia 35 is visible to a user who wishes to remove the garment 20 from the wearer. As used herein, the phrase "disposed on" when used with reference to the indicia 35 is used to mean that the informational indicia 35 is applied to, formed on, or otherwise provided with the tab member 31.

Figure 5A:
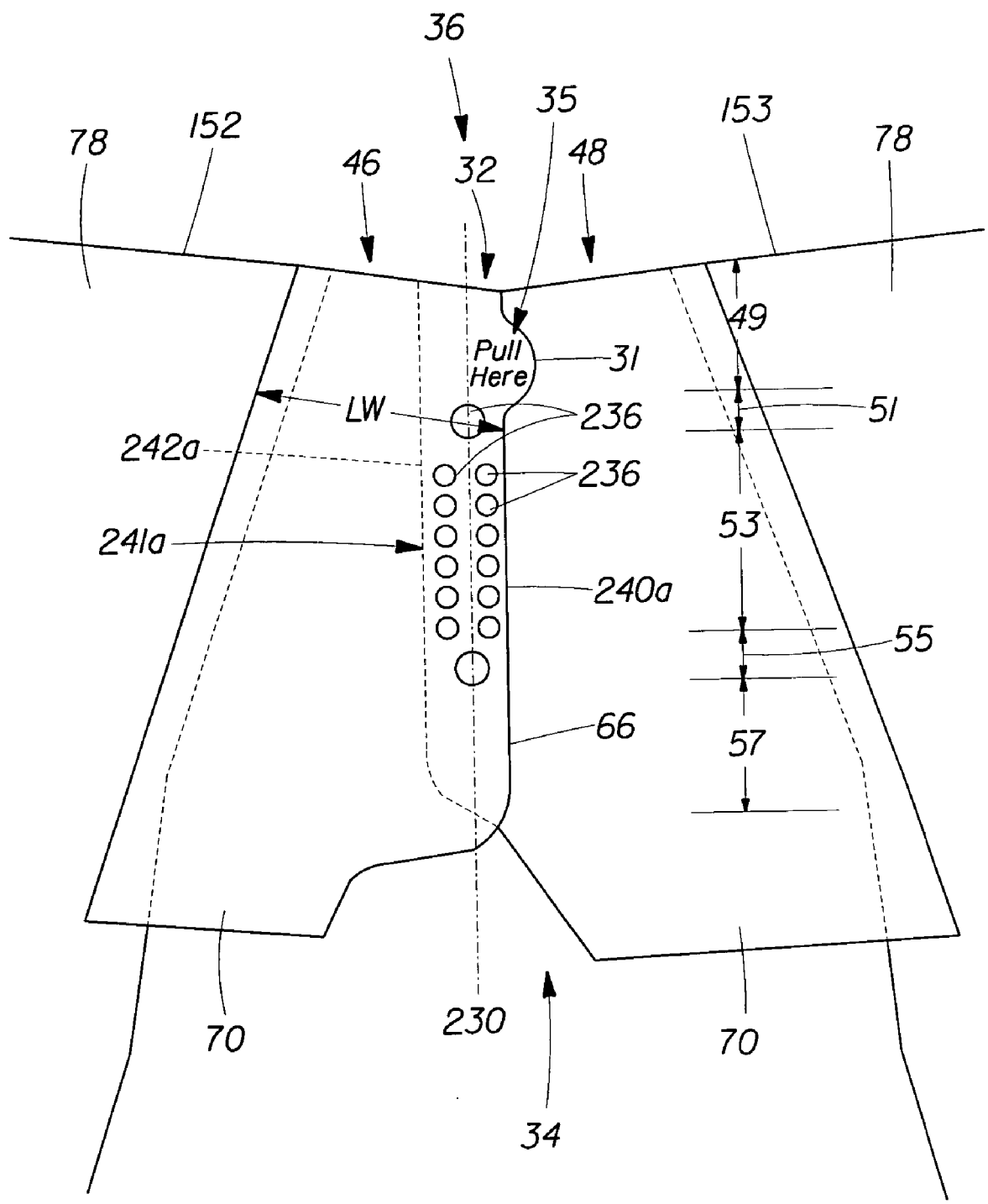
FIG. 5A is an enlarged plan view of a side seam joining the front and back ear panels similar to FIG. 4A, but presenting a tear-open tab carrying indicia in accordance with an alternative embodiment.
Figure 5B:
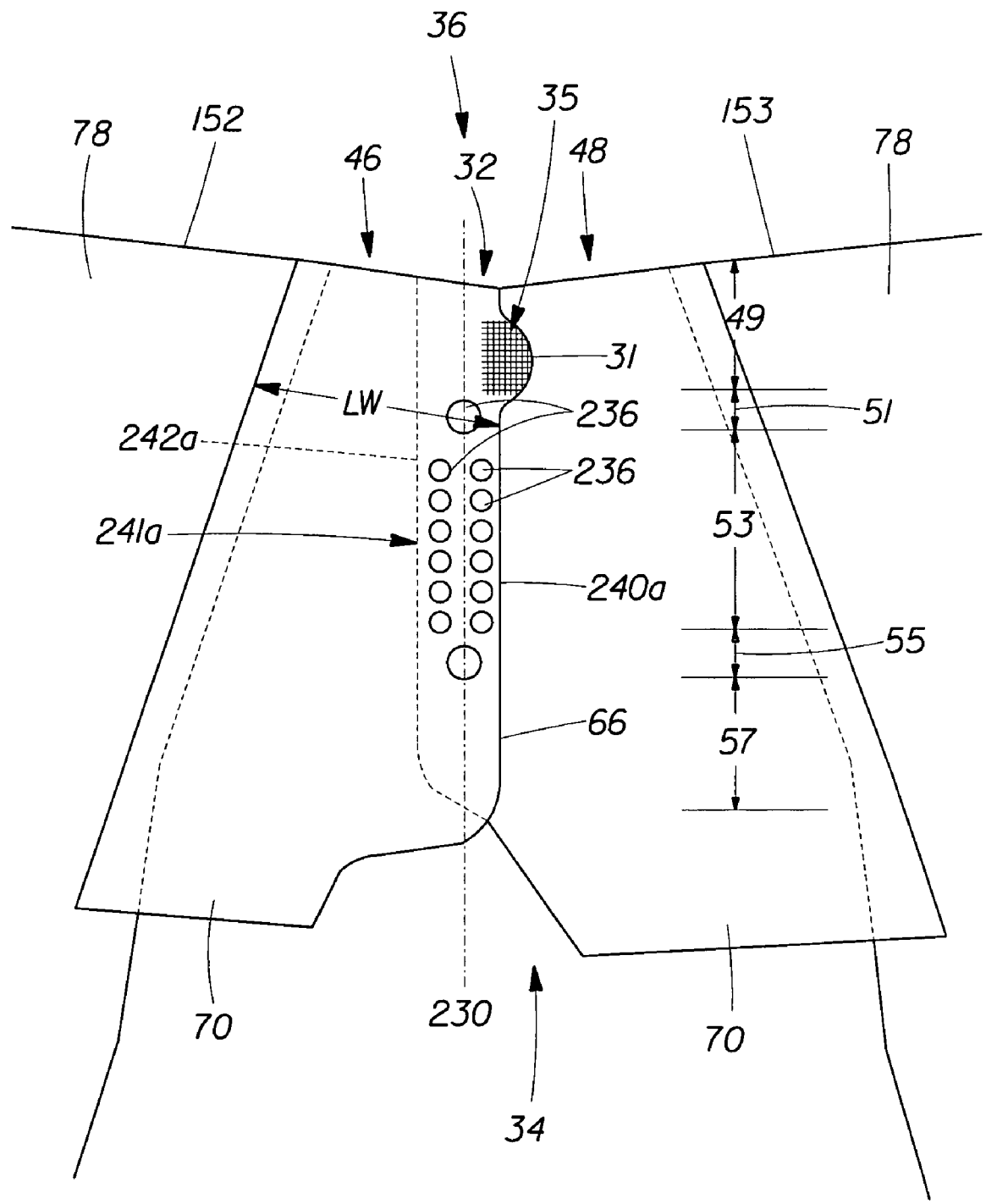
FIG. 5B is an enlarged plan view of a side seam joining the front and back ear panels similar to FIG. 5A, with the tear-open tab carrying indicia in accordance with another alternative embodiment.

Suitable indicia 35 can include graphics (such as the arrow shown in FIG. 4A), writing (e.g., "pull here" as shown in FIG. 5A or "open here" or other suitable language that communicates the use of the tab 31), regions that are colored differently than surrounding garment components, such as the chassis 41 (schematically shown in FIG. 5B), and combinations thereof that increase the visibility and intuitive use of the tab 31. Furthermore, the bond 236, the ear panels 46 and 48 (including one or more components thereof), the elastic member 70, the seam panels 66, and the closed side interface 241 generally can be colored differently or patterned differently, or carry other identifying indicia, that contrasts the various components, thereby increasing their visibility and communicating their intuitive use to the user. The term "communicate" as used herein refers to the ability of the informational image to impress an idea or message upon, or trigger a cognitive response within, a user. The indicia 35 can further include, but are not limited to, pictorial symbols, photographs, drawings, cartoons, and logos. The indicia 35 may be a single icon or a series of the same or different icons.

Figure 5C:
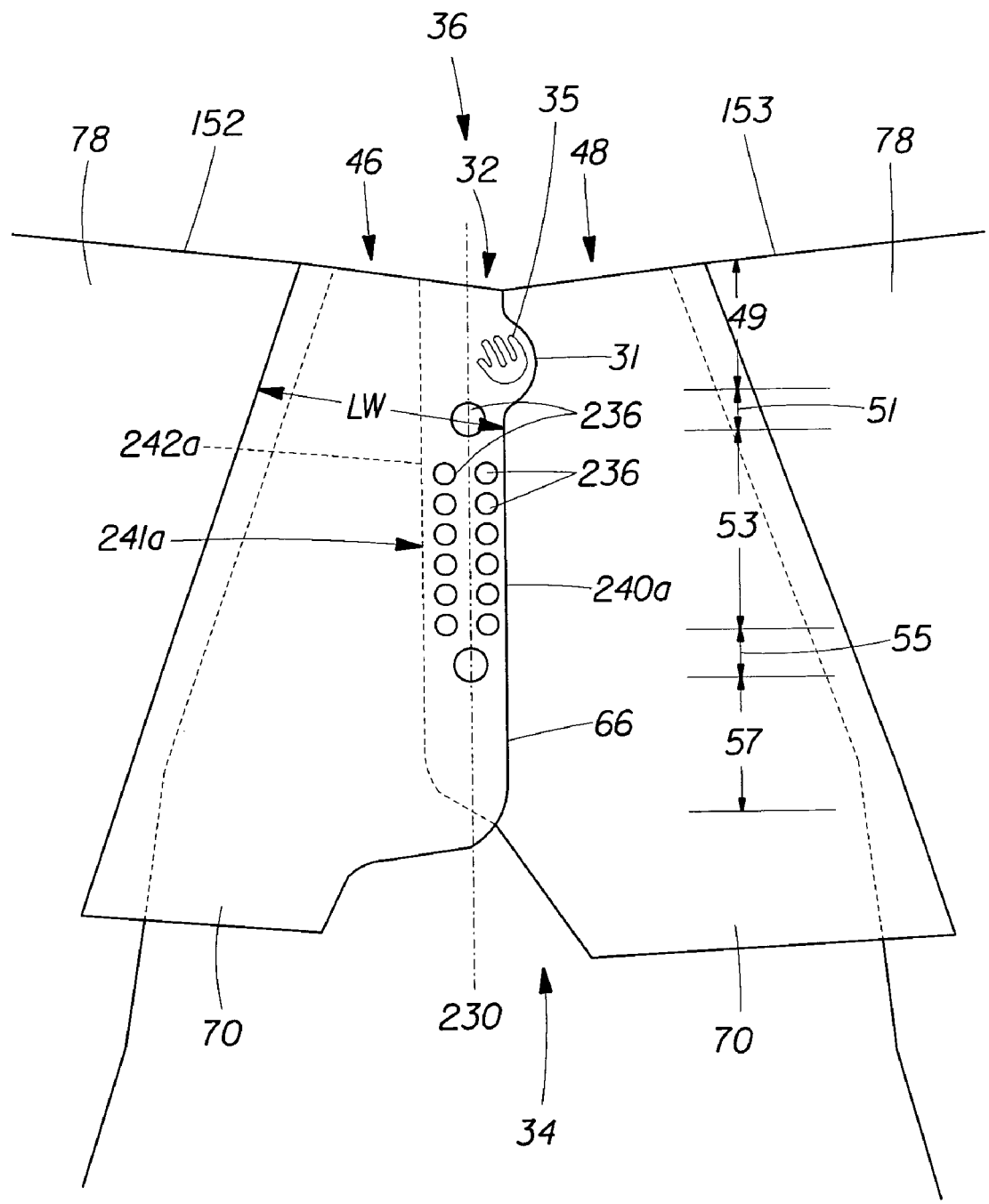
FIG. 5C is an enlarged plan view of a side seam joining the front and back ear panels similar to FIG. 5A, with the tear-open tab carrying indicia in accordance with another alternative embodiment.

Referring now to FIG. 5C, in another embodiment the indicia comprises a hand graphic to communicate to a user that the article is to be grasped in the location of the image. As used herein, the phrase "hand graphic" refers to an image formed to resemble a hand, a hand with a portion of an arm or body, or one or more portions thereof, such as a palm, one or more fingers, one or more fingertips, and the like.

Graphics other than the images described above can be used to attract a user's attention and indicate a gripping location, as described in U.S. patent application Ser. No. 11/038,606 and U.S. patent application Ser. No. 11/083,607, both filed on Mar. 18, 2005 by Donald C. Roe, et al.

When the seam 32 defines an overlapping configuration of the type described above, the tab 31 extends laterally outward from the outer edge (edge 240a as illustrated in FIG. 4A) of the exposed ear panel 46 that is exposed to the user when the garment 20 is worn. Accordingly, during use, the user can grab the opposing (or inner) ear panel 48 proximal the waist opening 36 with one hand, grab the tab 31 with the other hand, and apply the opening force with the tab 31 to open the seam 32 as described above.

Figure 7:
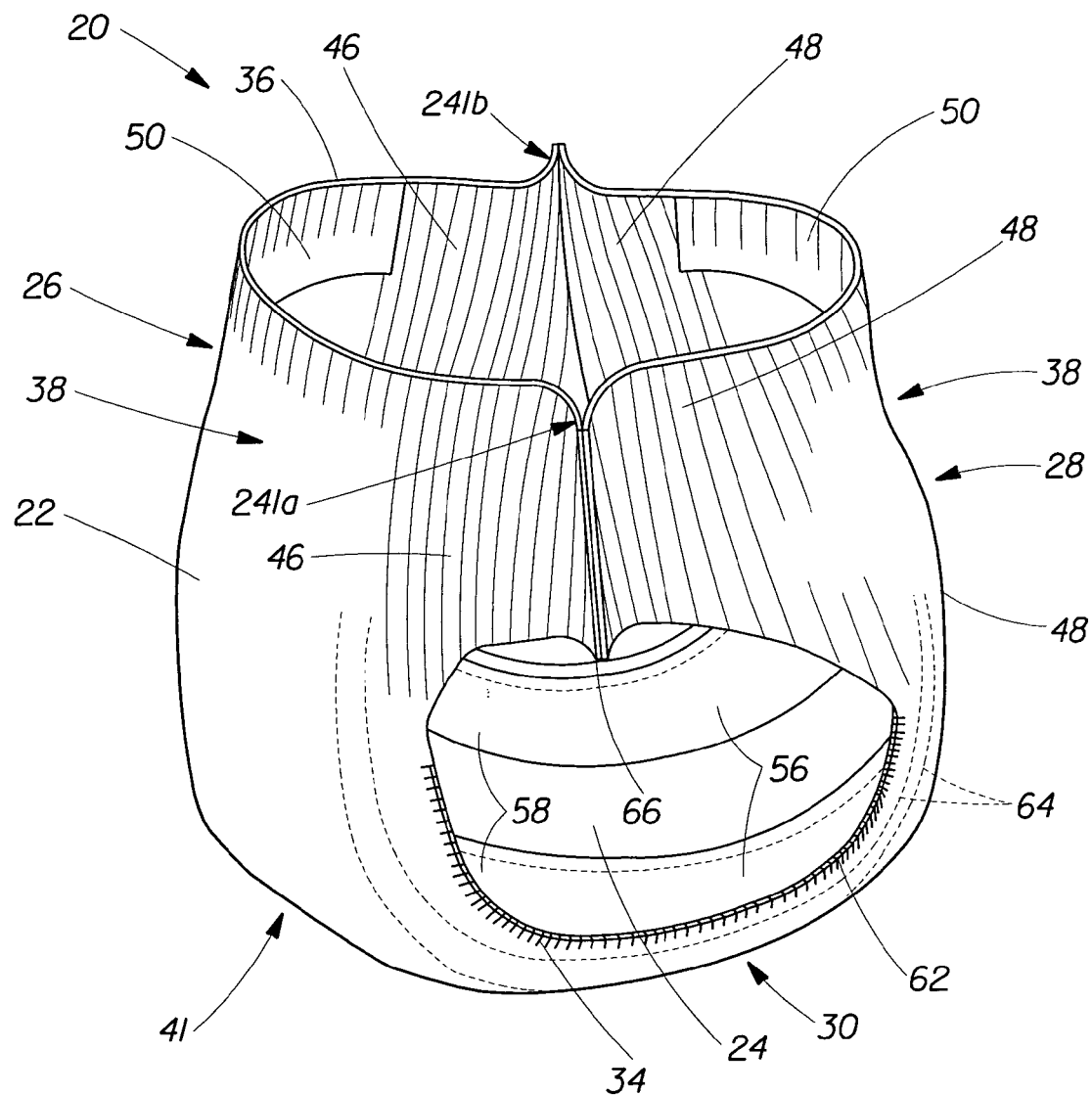
FIG. 7 is a perspective view of a disposable pull-on garment similar to that illustrated in FIG. 1, but with the side seams constructed in accordance with an alternative embodiment of the invention.

Alternatively, referring to FIG. 7, when the garment 20 defines a butt seam of the type described above, both outer edges 240 and 242 (see FIG. 2) can be exposed to the user, in which instance each ear panel 46 and 48 can be provided with tab 31 that each extends laterally outward from the outer edges 240a and 242a. Both tabs 31 can be individually grasped by the user, and pulled apart when applying the opening force.

Figure 6:
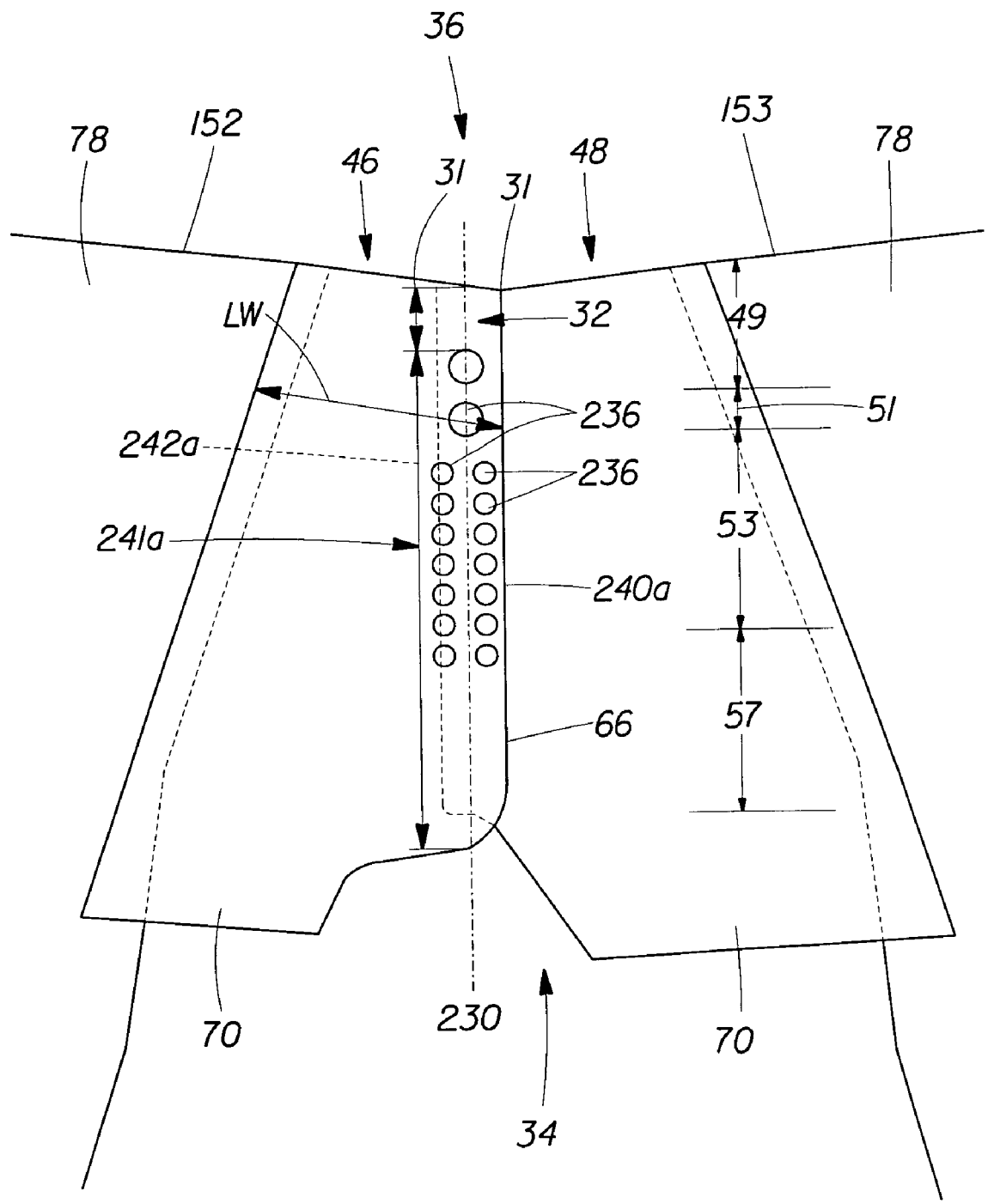
FIG. 6 is an enlarged plan view of the front and back ear panels similar to FIG. 4A but seamed in accordance with an alternative embodiment.

Alternatively still, as illustrated in FIG. 6, the tab 31 can extend longitudinally outward (or upward during use) from the outermost seam panel 66. The tab 31 can thus be said to be disposed proximal the upper end of the closed side interface 241a, and in vertical alignment with the seam 32 and the initiation region 49. It should be further appreciated that a pair of tabs 31 can extend longitudinally outward (or upward during use) from both ear panels 46 and 48 when the seam 32 is configured as an overlapping seam or as a butt seam.

Figure 14:
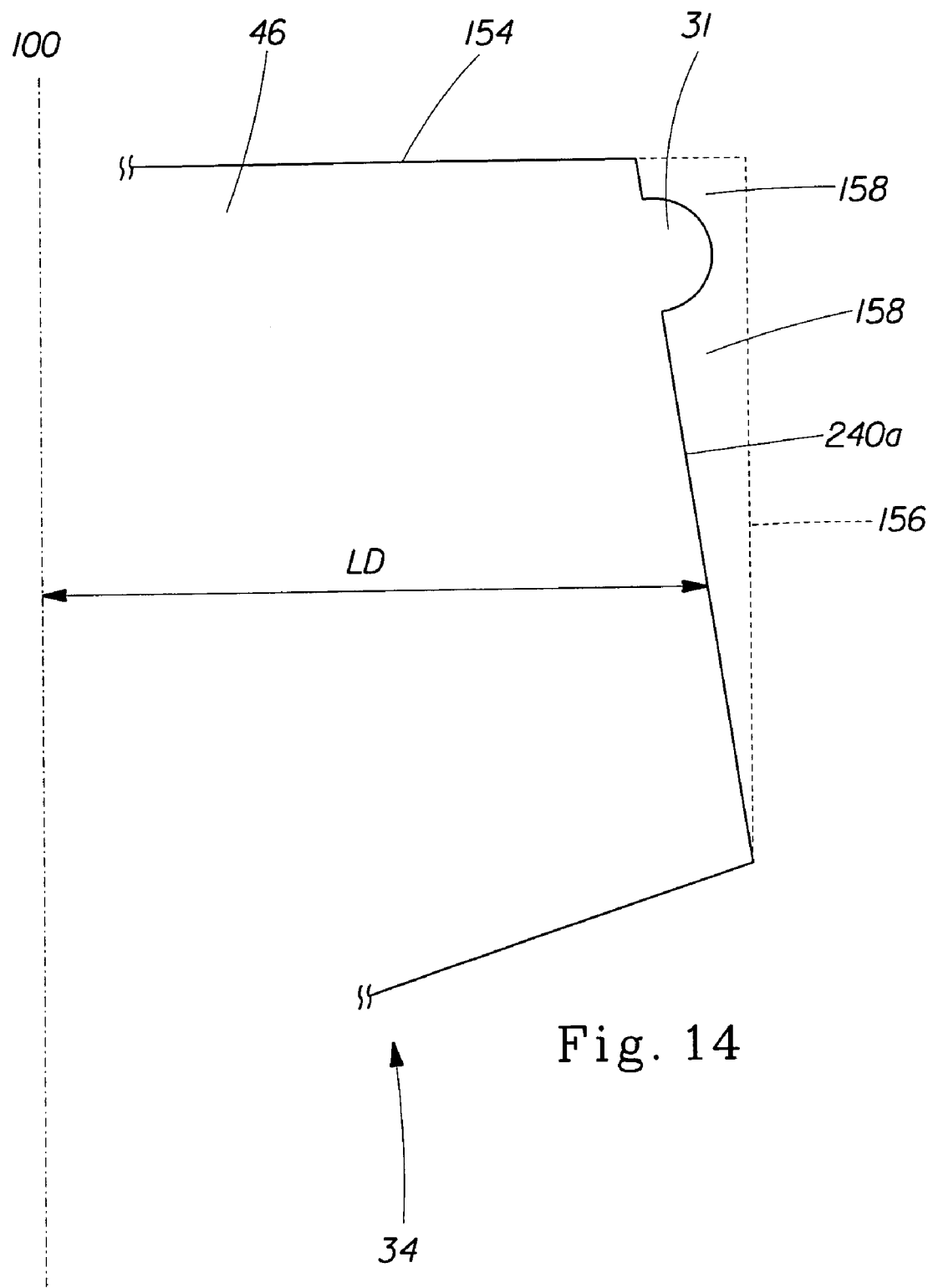
FIG. 14 is a plan view of the front ear panel constructed in accordance with certain aspects of the present invention.

Referring to FIG. 14, the tab member 31 can be constructed to be sufficiently strong while maximizes available material and minimizing waste. Because the lateral distance LD between the edge 240 and the longitudinal center line 100 increases towards the leg opening 34 as described above, the original material used to form the front ear panel 46 (illustrated in dashed lines) has a shape defined by the upper material line 154 and the side material line 156 which is perpendicular to the upper material line 154. The outer most edge 240 and the tear-open tab 31 are formed by removing (or cutting out) the edge portions 158 from the original material. Since the tear-open tab 31 can be obtained within the original material which has the right angle defined by the lines 154 and 156, an effective material use can be achieved (i.e., the original ear panel material can be used effectively). Furthermore, original material can be tucked under, or folded over, the tab 31 to increase tab strength and stiffness. It should further be appreciated that an additional layer or layers of materials, such as polymers, copolymers, adhesives, and cohesives, can be added to the upper or lower surface of the tab member 31, or between adjacent tab member layers to form a laminate that strengthens the tab member 31.

It should be appreciated that the tab 31 can extend from the closed side interface 241 as illustrated and described above, though it should be appreciated that the term "tab" as used herein includes an unbonded portion of the initiation region 49 so long as it can be discretely gripped by the user to open the seam 32.

The present invention recognizes that, when the user wishes to remove the garment 20 from the wearer (e.g., once the garment 20 has become soiled during use), the user can intuitively grip the tear-open tab 31 and apply the opening force that causes the bonds 236 to fail in sequence, thus opening the seam 32 and separating the ear panels 46 and 48. The garment 20 can then be easily removed from the wearer. The present invention recognizes that the type and magnitude of force applied by the user to each individual bond 236 will vary along the seam 32 in a direction from the waist opening 36 towards the leg opening 34

Figure 8A:
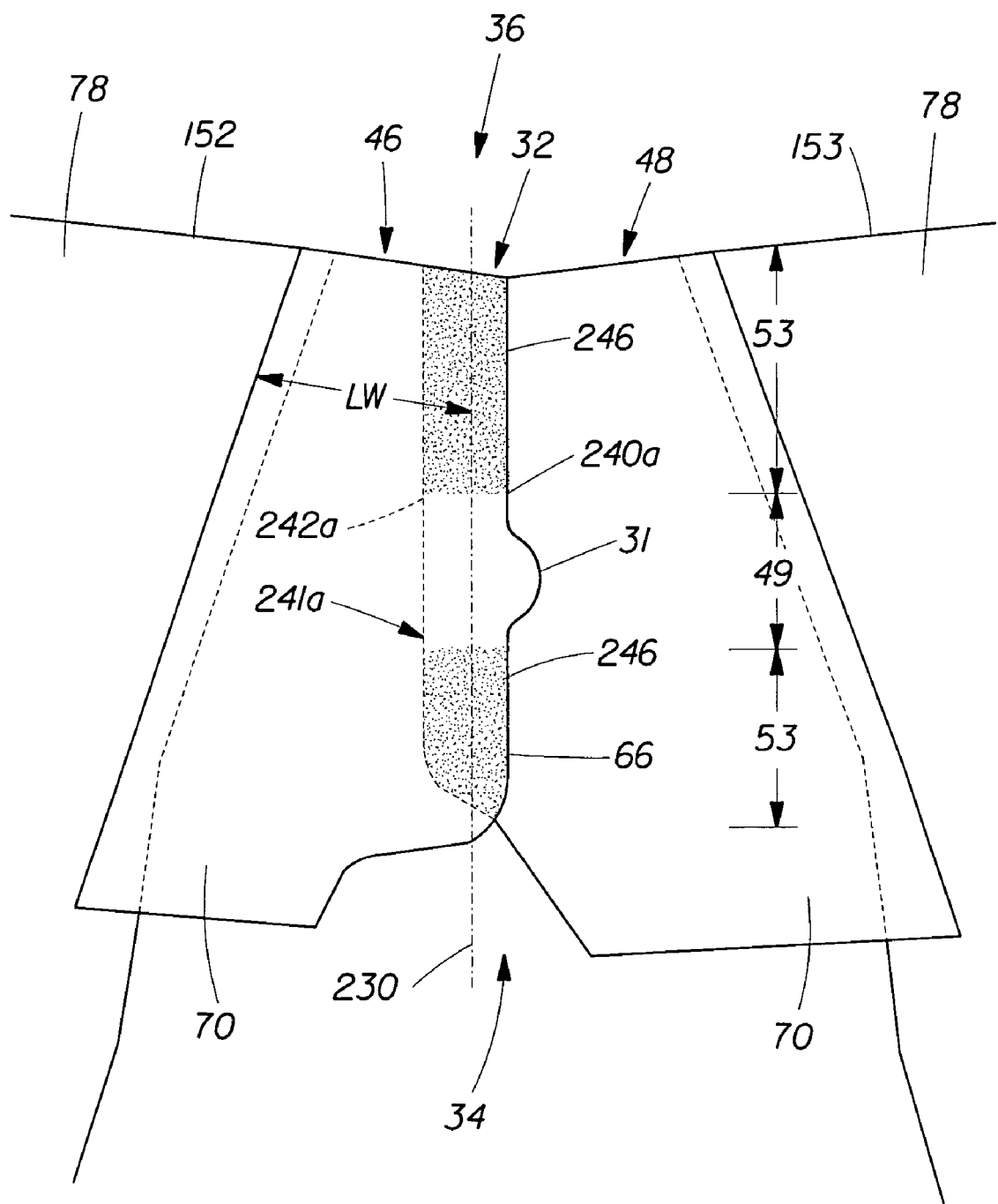
FIG. 8A is an enlarged plan view of a side seam joining the front and back ear panels similar to FIG. 4A, but with the side seam constructed in accordance with an alternative embodiment.
Figure 8B:
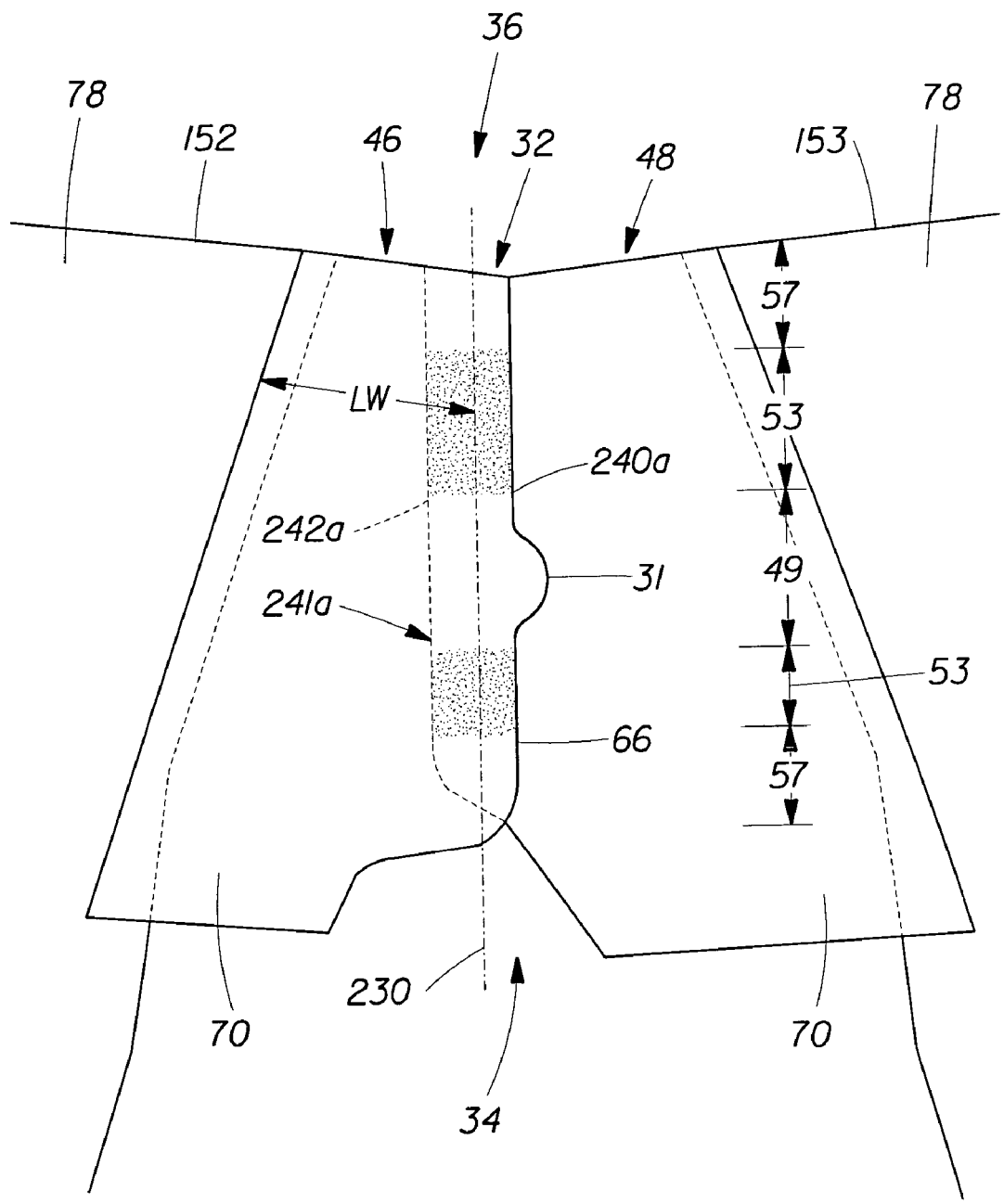
FIG. 8B is an enlarged plan view of a side seam joining the front and back ear panels similar to FIG. 8A, but constructed in accordance with an alternative embodiment.

Referring now to FIG. 8A, certain aspects of the present invention recognize that the tab 31 can extend from alternative locations while providing the enhanced leverage described above when opening the seam 32. For instance, as illustrated, the tab 31 extends from a middle portion of outer edge 240a. The term "middle portion" is used herein to refer to a position such that at least 20% of the vertical length of the seam 32 is disposed both above (i.e., in a direction toward the waist opening 36) and below (i.e., in a direction toward the corresponding leg opening 34) the tab 31. The tab 31 can be at least partially aligned with an initiation region 49 that can extend both above and below the tab 31. The initiation region 49 can be completely unbonded, or it can include low force bonds of the type described above. The remainder of the seam 32 (or at least portions of the seam 32) can be bonded using any suitable bond of the type described above. As illustrated, the seam panels 66 are connected via a hook-and-loop type fasteners 246, which extend between the initiation region 49 and the waist opening 36 at one end of the seam 32, and between the initiation region 49 and the leg opening 34 on the other side of the seam. The fasteners 246 can extend to the waist opening 36 and the leg opening 34 as illustrated in FIG. 8A or, as illustrated in FIG. 8B, the fasteners 246 can terminate short of the waist opening 36 and leg opening 34 such that an unbonded (or completion) region 55 extends between the leg opening 34 and the fastener 246, and/or between the waist opening 36 and the fastener 246. Hook-and-loop fasteners 246 have been recognized for their ability to provide adequate resistance to shear forces exerted on the seam 32 during use of the garment 20 while, at the same time, providing reliable separation in response to the user-applied opening force.

During use, when the user applies the opening force to the tab 31, the ear panels 46 and 48 separate at the initiation region 49, thereby providing an unbonded length of material that increases the opening force applied to the fastener 248. The opening force propagates along the fastener 248 in directions from the initiation region 49 toward the waist opening 36, and from the initiation region 49 toward the leg opening 34 (i.e., in propagation regions 53).

Figure 3:
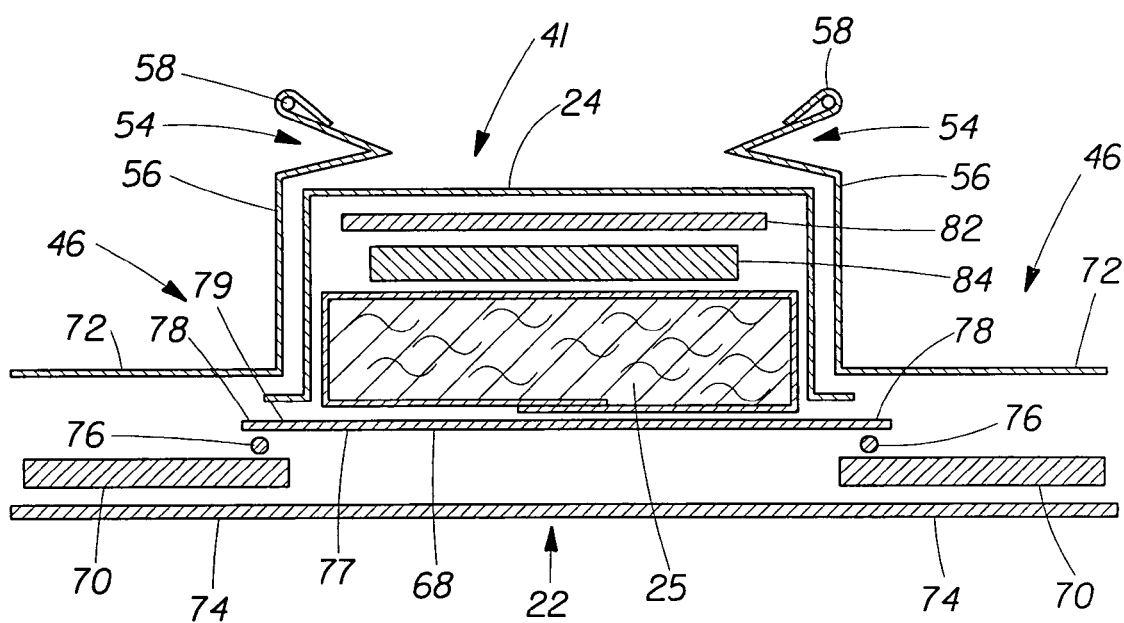
FIG. 3 is a cross-sectional view of the disposable pull-on garment illustrated taken along line 3-3 of FIG. 2.

Referring now to FIG. 3, the pull-on garment 20 includes the chassis 41 including the liquid previous topsheet 24, the liquid impervious backsheet 22 associated with the topsheet 24, and the absorbent core 25 positioned between the topsheet 24 and the backsheet 22. The pull-on garment further includes the front ear panels 46 each extending laterally outward from the chassis 41, and inner barrier leg cuffs 54. Although FIG. 3 depicts only the structure of the front ear panel 46 and the chassis 41 in the front waist region 26, a similar structure can also be provided in the back waist region 28. In one embodiment, each of the front ear panels 46 is formed by a lamination of an extended part 72 of the barrier flap 56, an elastic member 70 and the nonwoven outer cover 74. The elastic member 70 includes a plane elastomeric material 124 (see FIG. 11). Herein, "plane elastomeric material" refers to elastomeric materials which continuously extend in at least two dimensional directions. Exemplary elastomeric materials include a scrim, a perforated (or apertures formed) film, an elastomeric woven or nonwoven, and the like. In one embodiment, the plane elastomeric material 124 includes at least a portion that has a nonuniform lateral width.

FIG. 4A is a more detailed plan view of the front and back ear panels 46 and 48 shown in FIG. 1. Each of the ear panels 46 and 48 includes the elastic member 70 which includes a plane elastomeric material 124 (such as the one shown in FIG. 11). The elastic member 70 can further include an extensible sheet or film material (e.g., a nonwoven material) which is joined to the plane elastomeric material 124.

The plane elastomeric material 124 can define dimensions and have a shape identical to that of the elastic member 70. The elastic member 70 and the plane elastomeric material 124 can assume a wide variety of sizes and shapes (e.g., triangular, rectangular, other quadrilateral, and other polygon). The plane elastomeric material 124 has at least a portion that has a nonuniform lateral width LW that increases towards the leg opening 34 as shown in FIG. 4A. Alternatively, the lateral width LW of the plane elastomeric material 124 may decrease towards the leg opening 34.

Referring now to FIG. 1, a continuous belt 38 can be formed by the ear panels 46 and 48, and a part of the chassis 41 about the waist opening 36. Elasticized waist bands 50 can be provided in both the front waist region 26 and the back waist region 28. The continuous belt 38 acts to dynamically create fitment forces in the pull-on garment 20 when positioned on the wearer, to maintain the pull-on garment 20 on the wearer even when loaded with body exudates thus keeping the absorbent core 25 in close proximity to the wearer, and to distribute the forces dynamically generated during wear about the waist thereby providing supplemental support for the absorbent core 25 without binding or bunching the absorbent core 25.

Suitable absorbent materials for the absorbent core 25 are well-known and can comprise any absorbent material that is generally compressible, conformable, non-irritating to the wearer's skin, and capable of absorbing and retaining liquids such as urine and other certain body exudates. The absorbent core 250 may comprise a wide variety of liquid-absorbent materials commonly used in disposable diapers and other absorbent articles such as comminuted wood pulp, which is generally referred to as air felt. Examples of other suitable absorbent materials include creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. The absorbent core 250 can further comprise minor amounts (typically less than 10%) of non-liquid absorbent materials, such as adhesives, waxes, oils and the like. Exemplary absorbent structures for use as the absorbent assemblies are described in U.S. Pat. No. 4,610,678 (Weisman et al.); U.S. Pat. No. 4,834,735 (Alemany et al.); U.S. Pat. No. 4,888,231 (Angstadt); U.S. Pat. No. 5,260,345 (DesMarais et al.); U.S. Pat. No. 5,387,209 (Dyer et al.); U.S. Pat. No. 5,397,316 (LaVon et al.); U.S. Pat. No. 5,625,222 (DesMarais et al.). These absorbent materials can be used separately or in combination.

Many known absorbent materials can be used in a discrete form, i.e., in the form of fibers, granules, particles, and the like. Such a discrete form of an absorbent material can be immobilized by an adhesive that attaches the discrete pieces together to form a coherent layer or that attaches the discrete pieces to a substrate layer, such as a covering sheet, or that attaches the discrete pieces both to each other and to the substrate layer. Alternatively, the core 250 can comprise an absorbent polymer material in contact with a thermoplastic material. The absorbent polymer material can be further mixed with an absorbent fibrous material, such as airfelt material, or absorbent core 250 can be substantially airfelt free, as described in U.S. patent application Ser. No. 10/776, 851 (Becker et al), published as U.S. Publication. No. 2004/ 0162536.

In accordance with one aspect of the invention, the absorbent core 25 has, in the uncontracted state of the pull-on garment 20, an area ratio of the core area to the garment area of greater than about 25%, and alternatively greater than about 40%. The core area is defined as the total area of the body-facing surface of the absorbent core 25 in the uncontracted state of the pull-on garment 20. The periphery of the body-facing surface of the absorbent core 25 is determined by the outline of aggregates of primary absorbent materials used in the absorbent core 25. Herein, "primary absorbent material" refers to absorbent materials which occupy more than about 80% in dry state volume of the absorbent core 25. In one embodiment, a wood pulp (e.g., airfelt) is considered a primary absorbent material of the absorbent core 25 and defines the periphery of the body-facing surface of the absorbent core 25, thus defining the core area of the absorbent core 25. The other primary absorbent materials may include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

The garment area is defined as the total area of the body-facing surface of the pull-on garment 20 in the uncontracted state. Therefore, the area ratio is calculated as follows:

$$AR = CA/GA \times 100$$

wherein,
AR: the area ratio (%)
CA: the core area (cm$^2$)
GA: the total area (cm$^2$)

In one embodiment particularly suitable for infant use, the absorbent core 25 has a core area of less than about 450 cm$^2$, and alternatively less than about 425 cm$^2$. The absorbent core 25 an have a maximum core width (i.e., the lateral distance from one side edge to the opposing side edge of the absorbent core 25) of less than about 12 cm, and alternatively less than about 11 cm.

The configuration and construction of the absorbent core 25 may vary (e.g., the absorbent core 25 may have varying caliper zones, a hydrophilic gradient, a superabsorbent gradient, or lower average density and lower average basis weight acquisition zones; or may include one or more layers or structures). Further, the size and absorbent capacity of the absorbent core 25 may also be varied to accommodate wearers ranging from infants through adults. However, the total absorbent capacity of the absorbent core 25 should be compatible with the design loading and the intended use of the garmnent 20.

The garment 20 can define an asymmetric, modified hourglass-shaped absorbent core 25 having ears in the front and back waist regions 26 and 28. Other exemplary absorbent structures for use as the absorbent core 25 that have achieved wide acceptance and commercial success are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989.

The chassis 41 may further include an acquisition/distribution core 84 of chemically stiffened fibers positioned over the absorbent core 25, thereby forming a dual core system. The fibers can be hydrophilic chemically stiffened cellulosic fibers, meaning that the cellulosic fibers have been stiffened by chemical means to increase stiffness of the fibers under both dry and aqueous conditions. Such means include the addition of chemical stiffening agents which, for example, coat and/or impregnate the fibers. Such means also include the stiffening of the fibers by altering the chemical structure of the fibers themselves, e.g., by cross-linking polymer chains.

The fibers utilized in the acquisition/distribution core 84 can also be stiffened by means of chemical reaction. For example, crosslinking agents can be applied to the fibers which, subsequent to application, are caused to chemically form intrafiber crosslink bonds. These crosslink bonds can increase stiffness of the fibers. Whereas the utilization of intrafiber crosslink bonds to chemically stiffen the fibers is preferred, it is not meant to exclude other types of reactions for chemical stiffening of the fibers.

In the more preferred stiffened fibers, chemical processing includes intrafiber crosslinking with crosslinking agents while such fibers are in a relatively dehydrated, defibrated (i.e. individualized), twisted, curled condition. Suitable chemical stiffening agents include monomeric crosslinking agents including, but not limited to, $C_2$-$C_8$ dialdehydes and $C_2$-$C_8$ monoaldehydes having an acid functionality can be employed to form the crosslinking solution. These compounds are capable of reacting with at least two hydroxyl groups in a single cellulose chain or on proximately located cellulose chains in a single fiber. Such crosslinking agents contemplated for use in preparing the stiffened cellulose fibers include, but are not limited to, glutaraldehyde, glyoxal, formaldehyde, and glyoxylic acid. Other suitable stiffening agents are polycarboxylates, such as citric acid. The polycarboxylic stiffening agents and a process for making stiffened fibers from them are described in U.S. Pat. No. 5,190,563, entitled "Process for Preparing Individualized, Polycarboxylic Acid crosslinked Fibers" issued to Herron, on Mar. 2, 1993. The effect of crosslinking under these conditions is to form fibers which are stiffened and which tend to retain their twisted, curled configuration during use in the absorbent articles herein. Such fibers, and processes for making them are cited in the above incorporated patents.

Exemplary dual core systems are disclosed in U.S. Pat. No. 5,234,423, entitled "Absorbent Article With Elastic Waist Feature and Enhanced Absorbency" issued to Alemany et al., on Aug. 10, 1993; and in U.S. Pat. No. 5,147,345, entitled "High Efficiency Absorbent Articles For Incontinence Management" issued to Young, LaVon and Taylor on Sep. 15, 1992. In one embodiment, the acquisition/distribution core 84 includes chemically treated stiffened cellulosic fiber material, available from Weyerhaeuser Co. (U.S.A.) under the trade designation of "CMC". The acquisition/distribution core 84 can have a basis weight of from about 40 g/m$^2$ to about 400 g/m$^2$, and alternatively from about 75 g/m$^2$ to about 300 g/m$^2$.

The chassis 22 can further include an acquisition/distribution layer 82 disposed between the topsheet 24 and the acquisition/distribution core 84 as shown in FIG. 3. The acquisition/distribution layer 82 is provided to help reduce the tendency for surface wetness of the topsheet 24. The acquisition/distribution layer 82 includes carded, resin bonded hiloft nonwoven materials such as, for example, those available as Code No. FT-6860 from Polymer Group, Inc., North America (Landisiville, N.J., U.S.A.), which is made of polyethylene telephthalate fibers of 6 dtex, and has a basis weight of about 43 g/m$^2$. One example for the acquisition/distribution layer 82 and the acquisition/distribution core 84 is disclosed in EP 0797968A1 (Kurt et al.) published on Oct. 1, 1997.

The topsheet 24 is can be compliant, soft feeling, and non-irritating to the wearer's skin. Further, the topsheet 24 is liquid pervious permitting liquids (e.g., urine) to readily penetrate through its thickness. A suitable topsheet 24 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be included of natural fibers (e.g., wood or cotton fibers), synthetic fibers (e.g., polymeric fibers such as polyester, polypropylene, or polyethylene fibers) or from a combination of natural and synthetic fibers. The topsheet 24 is made of a hydrophobic material to isolate the wearer's skin from liquids which have passed through the topsheet 24 and are contained in the absorbent core 25 (i.e., to prevent rewet). If the topsheet 24 is made of a hydrophobic material, at least the upper surface of the topsheet 24 is treated to be hydrophilic so that liquids will transfer through the topsheet more rapidly. This diminishes the likelihood that body exudates will flow off the topsheet 24 rather than being drawn through the topsheet 24 and being absorbed by the absorbent core 25. The topsheet 24 can be rendered hydrophilic by treating it with a surfactant. Suitable methods for treating the topsheet 24 with a surfactant include spraying the topsheet 24 material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al. on Jan. 29, 1991 and U.S. Pat. No. 4,988,345 entitled "Absorbent Articles with Rapid Acquiring Absorbent Cores" issued to Reising on Jan. 29, 1991.

In one embodiment, the topsheet 24 is a nonwoven web that can provide reduced tendency for surface wetness; and consequently facilitate maintaining urine absorbed by the core 25 away from the user's skin, after wetting. One exemplary material is a thermobonded carded web which is available as Code No. P-8 from Fiberweb North America, Inc. (Simpsonville, S.C., U.S.A.). Another exemplary topsheet material is available as Code No. S-2355 from Havix Co., Japan. This material is a bi-layer composite material, and made of two kinds of synthetic surfactant treated bicomponent fibers by using carding and air-through technologies. Yet another exemplary topsheet material is a thermobonded carded web which is available as Code No. Profleece Style 040018007 from Amoco Fabrics, Inc. (Gronau, Germany).

In one embodiment, the topsheet 24 is compatible with other materials (e.g., component materials in the backsheet 22) used in the pull-on garment 20 or 120, in terms of its design/process, for forming ventilation holes along the waist edges 152 and 153 and/or at other portions of the pull-on garment 20 or 120.

Another exemplary topsheet 24 includes an apertured formed film. Apertured formed films have the property of being pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", issued to Thompson on Dec. 30, 1975; U.S. Pat. No. 4,324,246 entitled "Disposable Absorbent Article Having A Stain Resistant Topsheet", issued to Mullane, et al. on Apr. 13, 1982; U.S. Pat. No. 4,342,314 entitled "Resilient Plastic Web Exhibiting Fiber-Like Properties", issued to Radel. et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", issued to Ahr et al. on Jul. 31, 1984; and U.S. Pat. No. 5,006,394 "Multilayer Polymeric Film" issued to Baird on Apr. 9, 1991.

The backsheet 22 can include a liquid impervious film 68 as shown in FIG. 3. The liquid impervious film 68 extends longitudinally in the front, back and crotch regions 26, 28 and 30. The liquid impervious film 68 does not extend laterally into the at least one of the ear panels 46 or 48. The liquid impervious film 68 has a body-facing surface 79 and an outer-facing surface 77. The liquid impervious film 68 is impervious to liquids (e.g., urine) and is can be manufactured from a thin plastic film that permits vapors to escape from the garment 20. As an example, a microporous polyethylene film is used for the liquid impervious film 68. A suitable microporous polyethylene film is manufactured by Mitsui Toatsu Chemicals, Inc., Nagoya, Japan and marketed in the trade as PG-P. A disposable tape (not shown) can be additionally joined to the outer surface of the backsheet 22 to provide a convenient disposal after soiling.

A suitable material for the liquid impervious film 68 is a thermoplastic film having a thickness of from about 0.012 mm (0.5 mil) to about 0.051 mm (2.0 mils), that can include polyethylene or polypropylene. The liquid impervious film can have a basis weight of from about 5 g/m$^2$ to about 35 g/m$^2$. However, it should be noted that other flexible liquid impervious materials may be used. Herein, "flexible" refers to materials which are compliant and which will readily conform to the general shape and contours of the wearer's body.

The backsheet 22 can further include the nonwoven outer cover 74 which is joined with the outer-facing surface of the liquid impervious film 68 to form a laminate (i.e., the backsheet 22). The nonwoven outer cover 74 is positioned at the outermost portion of the garment 20 and covers at least a portion of the outermost portion of the garment 20. In accordance with one embodiment, the nonwoven outer cover 74 covers almost all of the area of the outermost portion of the garment 20. The nonwoven outer cover 74 may be joined to the liquid impervious film 68 by any suitable attachment means known in the art. For example, the nonwoven outer cover 74 may be secured to the liquid impervious film 68 by a uniform continuous layer of adhesive, a patterned layer of adhesive, or an array of separate lines, spirals, or spots of adhesive. Suitable adhesives include a hotmelt adhesive obtainable from Nitta Findley Co., Ltd., Osaka, Japan as H-2128, and a hotmelt adhesive obtainable from H. B. Fuller Japan Co., Ltd., Osaka, Japan as JM-6064.

The nonwoven outer cover 74 can be a carded nonwoven web, for example, obtainable from Havix Co., LTD., Gifu, Japan as E-2341. The nonwoven outer cover 74 is made of bi-component fibers of a polyethylene (PE) and a polypropylene (PP). The ratio of PE/PP is about 50/50. The PE/PP bi-component fiber has the dimension of 2 d.times.51 mm. Another carded nonwoven web is obtainable from Chisso Corp., Moriyama, Japan. The nonwoven outer cover 74 is also made of bi-component fibers of a polyethylene (PE) and a polypropylene (PP). The ratio of PE/PP is about 50/50.

In another embodiment, the nonwoven web is a spunbonded nonwoven web, for example, obtainable from Mitsui Petrochemical Industries, Ltd., Tokyo, Japan. The nonwoven web is made of bi-component fibers of a polyethylene (PE) and a polypropylene (PP). The ratio of PE/PP is about 80/20. The PE/PP bi-component fiber has the thickness is approximately 2.3 d.

The backsheet 22 can be rendered compatible with other materials (e.g., component materials in the topsheet 24) used in the pull-on garment 20 or 120, in terms of its design/process, for forming ventilation holes along the waist edges 152 and 153 and/or for forming seams 32 in the pull-on garment 20 or 120.

The backsheet 22 is positioned adjacent the outer-facing surface of the absorbent core 25 and is joined thereto by any suitable attachment mechanism known in the art. For example, the backsheet 22 may be secured to the absorbent core 25 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn., U.S.A., and marketed as HL-1358J. An example of a suitable attachment means including an open pattern network of filaments of adhesive is disclosed in U.S. Pat. No. 4,573,986 entitled "Disposable Waste-Containment Garment", which issued to Minetola et al. on Mar. 4, 1986. Another suitable attachment means including several lines of adhesive filaments swirled into a spiral pattern is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Alternatively, the attachment means may include discrete heat bonds, pressure bonds, ultrasonic bonds, dynamic mechanical bonds, or any other suitable attachment means or combinations of these attachment means as are known in the art.

In an alternative embodiment, the absorbent core 25 is not joined to the backsheet 22, and/or the topsheet 24 in order to provide greater extensibility in the front waist region 26 and the back waist region 28.

The pull-on garment 20 can further include elasticized leg cuffs 52 that provide improved containment of liquids and other body exudates. The elasticized leg cuffs 52 may include several different embodiments for reducing the leakage of body exudates in the leg regions. (The leg cuffs can be and are sometimes also referred to as leg bands, side flaps, barrier cuffs, elastic cuffs or gasketing cuffs.) U.S. Pat. No. 3,860,003 entitled "Contractable Side Portions for Disposable Diaper" issued to Buell on Jan. 14, 1975, describes a disposable diaper which provides a contractible leg opening having a side flap and one or more elastic members to provide an elasticized leg cuff. U.S. Pat. No. 4,909,803 entitled "Disposable Absorbent Article Having Elasticized Flaps" issued to Aziz et al. on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987; and U.S. Pat. No. 4,795,454 entitled "Absorbent Article Having Leakage-Resistant Dual Cuffs" issued to Dragoo on Jan. 3, 1989, describe disposable diapers having dual cuffs including a gasketing cuff and a barrier cuff. U.S. Pat. No. 4,704,115 entitled "Disposable Waist Containment Garment" issued to Buell on Nov. 3, 1987, discloses a disposable diaper or incontinence garment having side-edge-leakage-guard gutters configured to contain free liquids within the garment.

While each elasticized leg cuff 52 may be configured so as to be similar to any of the leg bands, side flaps, barrier cuffs, or elastic cuffs described above, one aspect of the invention provides for the elasticized leg cuff 52 including an elastic gasketing cuff 62 with one or more elastic strands 64 as shown in FIG. 2, which is described in the above-referred U.S. Pat. Nos. 4,695,278 and 4,795,454. Each elasticized leg cuff 52 can further include inner barrier cuffs 54 each including a barrier flap 56 and a spacing means 58 which are described in the above-referenced U.S. Pat. No. 4,909,803.

The pull-on garment 20 can further include an elasticized waistband 50 that provides improved fit and containment. The elasticized waistband 50 is that portion or zone of the pull-on garment 20 which is intended to elastically expand and contract to dynamically fit the wearer's waist. The elasticized waistband 50 can extend longitudinally outwardly from the waist edge of the pull-on garment 20 toward the waist edge of the absorbent core 25. The pull-on garment 20 has two elasticized waistbands 50, one positioned in the back waist region 28 and one positioned in the front waist region 26, although other pull-on diaper embodiments can be constructed with a single elasticized waistband. The elasticized waistband 50 may be constructed in a number of different configurations including those described in U.S. Pat. No. 4,515,595 entitled "Disposable Diapers with Elastically Contractible Waistbands" issued to Kievit et al. on May 7, 1985 and the above referenced U.S. Pat. No. 5,151,092 issued to Buell.

The waistbands 50 may include materials that have been "prestrained" or "mechanically prestrained" (i.e., subjected to some degree of localized pattern mechanical stretching to permanently elongate the material). The materials may be prestrained using deep embossing techniques as are known in the art. Alternatively, the materials may be prestrained by directing the material through an incremental mechanical stretching system as described in U.S. Pat. No. 5,330,458 entitled "Absorbent Article With Elastic Feature Having A Portion Mechanically Prestrained" issued to Buell et al., on Jul. 19, 1994. The materials are then allowed to return to their substantially untensioned condition, thus forming a zero strain stretch material that is extensible, at least up to the point of initial stretching. Examples of zero strain materials are disclosed in U.S. Pat. No. 2,075,189 issued to Galligan on Mar. 30, 1937; U.S. Pat. No. 3,025,199 issued to Harwood on Mar. 13, 1962; U.S. Pat. Nos. 4,107,364 and 4,209,563 issued to Sisson on Aug. 15, 1978 and Jun. 24, 1980, respectively; U.S. Pat. No. 4,834,741 issued to Sabee on May 30, 1989; and U.S. Pat. No. 5,151,092 issued to Buell et al., on Sep. 29, 1992.

As described above with reference to FIG. 3, at least one of the ear panels 46 and 48 includes the elastic member 70 as shown in FIG. 3. The elastic member 70 of the front ear panels 46 includes the elastomeric material 124 (see FIG. 11) which extends laterally outward from the chassis 41 to provide good fitness by generating the optimal retention (or sustained) force at the waist and side areas of the wearer. The elastomeric material 124 can be extensible in at least one direction, for example the lateral direction, to generate a retention (or sustained) force that is optimal to prevent the pull-on garment 20 from drooping, sagging, or sliding down from its position on the torso without causing the red marking on the skin of the wearer. It should be appreciated that each of the ear panels 46 and 48 can include the elastomeric material 124. It should be appreciated that any one of layers 72, 70, and 74 (for instance the elastic member 70) could terminate prior to the seam 32 if desired.

The elastic member 70 is operatively joined to at least one of the nonwoven webs 72 and 74 in the ear panels 46 and 48 to allow the elastic member 70 to be elastically extensible in at least the lateral direction. The elastic member 70 can be operatively joined to the nonwoven webs 72 and 74 by securing them to at least one, or both, of the nonwoven webs 72 and 74 while in a substantially untensioned (zero strain) condition.

The elastic member 70 can be operatively joined to the nonwoven webs 72 and 74, by using either an intermittent bonding configuration or a substantially continuous bonding configuration. Herein, "intermittently" bonded laminate web means a laminate web wherein the plies are initially bonded to one another at discrete spaced apart points or a laminate web wherein the plies are substantially unbonded to one another at discrete spaced apart areas. Conversely, a "substantially continuously" bonded laminate web means a laminate web wherein the plies are initially bonded substantially continuously to one another throughout the areas of interface. It may be desired that the stretch laminate be bonded over all or a significant portion of the stretch laminate so that the inelastic webs (i.e., the nonwoven webs 72 and 74) elongate or draw without causing rupture, and the layers of the stretch laminates are bonded in a configuration that maintains all of the layers of the stretch laminate in relatively close adherence to one another after the incremental mechanical stretching operation. Consequently, the elastic panel members and the other plies of the stretch laminate are substantially continuously bonded together using an adhesive. In one embodiment, the adhesive selected is applied with a control coat spray pattern at a basis weight of about 7.0 grams/square m. The adhesive pattern width is about 6.0 cm. The adhesive can be of the type available from Nitta Findley Co., Ltd., Osaka, Japan, under the designation H2085F. Alternatively, the elastic panel member and any other components of the stretch laminates may be intermittently or continuously bonded to one another using heat bonding, pressure bonding, ultrasonic bonding, dynamic mechanical bonding, or any other method as is known in the art.

After the elastic member 70 is operatively joined to at least one of the nonwoven webs 72 and 74, at least a portion of the resultant composite stretch laminate is then subjected to mechanical stretching sufficient to permanently elongate the non-elastic components which are, for example, the nonwoven webs 72 and 74. The composite stretch laminate is then allowed to return to its substantially untensioned condition. At least one pair of, alternatively both of, the ear panels 46 and 48 is thus formed into "zero strain" stretch laminates. (Alternatively, the elastic member 70 could be operatively joined in a tensioned condition and then subjected to mechanical stretching.) Herein, "zero strain" stretch laminate refers to a laminate included of at least two plies of material which are secured to one another along at least a portion of their coextensive surfaces while in a substantially untensioned ("zero strain") condition; one of the plies including a material which is stretchable and elastomeric (i.e., will return substantially to its untensioned dimensions after an applied tensile force has been released) and a second ply which is elongatable (but not necessarily elastomeric) so that upon stretching the second ply will be, at least to a degree, permanently elongated so that upon release of the applied tensile forces, it will not fully return to its original undeformed configuration. The resulting stretch laminate is thereby rendered elastically extensible, at least up to the point of initial stretching, in the direction of initial stretching. Suitable methods and apparatus used for making stretch laminates utilize meshing corrugated rolls to mechanically stretch the components. Suitable apparatus and methods are disclosed in U.S. Pat. No. 5,167,897 issued to Weber et al. on Dec. 1, 1992; U.S. Pat. No. 5,156,793 issued to Buell et al. on Oct. 20, 1990; and U.S. Pat. No. 5,143,679 issued to Weber et al. on Sep. 1, 1992.

The elastic member 70 can be joined to, or directly secured to, the respective edges 78 of the liquid impervious film (i.e., the liquid impervious film 68), through an adhesive 76 as shown in FIG. 3. While liquid impervious film 68 longitudinally extends in the front, back and crotch regions 26, 28 and 30, it need not laterally extend into at least one of, or each of, the extensible ear panels 46 and 48. In one embodiment, the elastic member 70 is joined to the respective edges 78 of the liquid impervious film 68 at the outer-facing surface 77 as shown in FIG. 3. In an alternative embodiment, the elastic member 70 may be joined to the respective edges 78 of the liquid impervious film 68 at the body-facing surface 79. The adhesive 76, which can be a flexible adhesive with an amorphous and crystallizing component, can be applied in a spiral glue pattern. Such an adhesive is made by Nitta Findley Co., Ltd., Osaka, Japan, under the designation H2085F. Alternatively, the elastic member 70 may be joined to the respective edges 78 of the liquid impervious film 68 by any other bonding means known in the art which include heat bonds, pressure bonds, ultrasonic bonds, dynamic mechanical bonds, or combinations of these attachment means.

Figure 9:
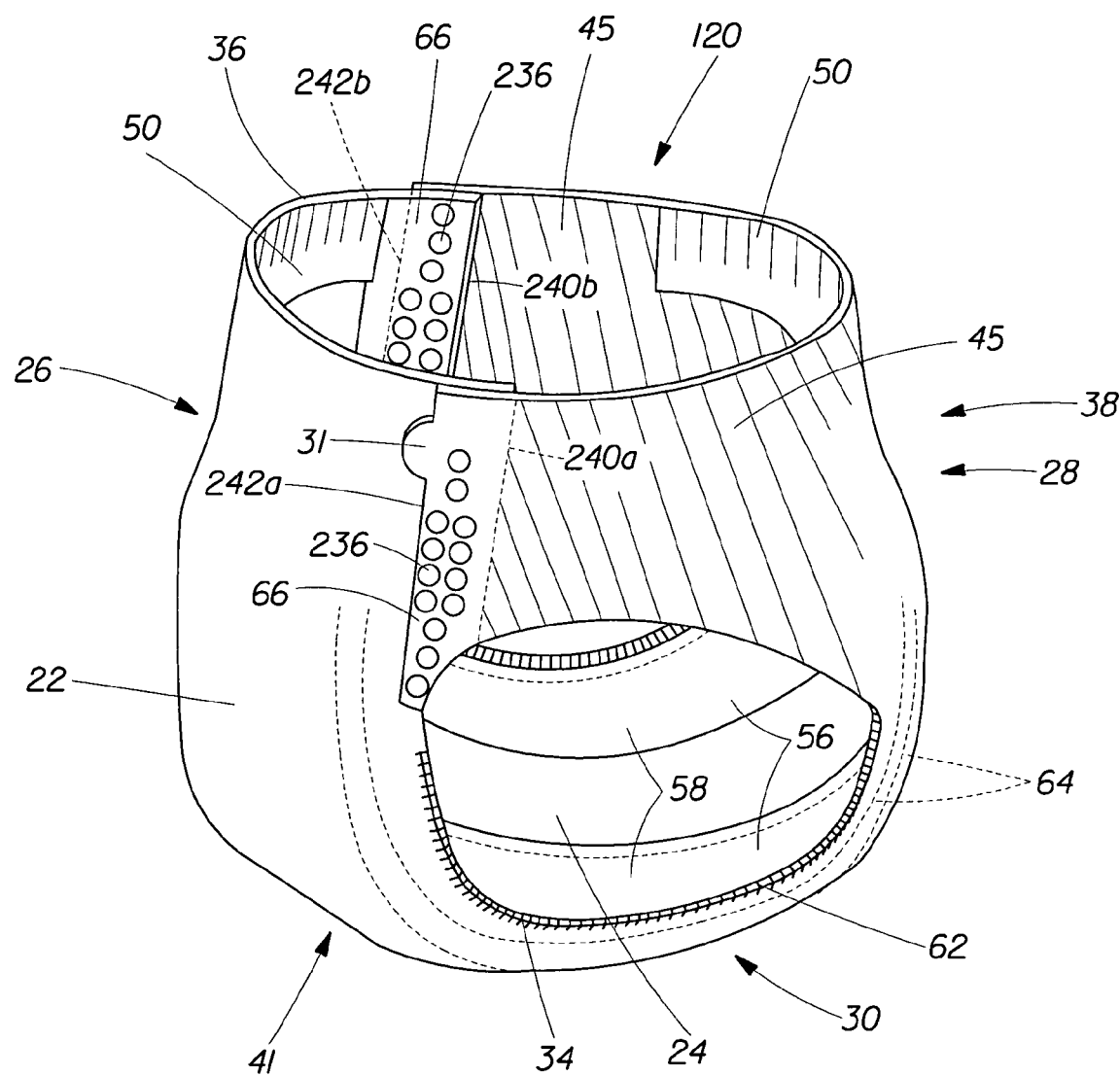
FIG. 9 is a perspective view of a disposable pull-on garment similar to FIG. 1, but with the garment constructed in accordance with an alternative embodiment.

Referring to FIG. 9, a pull-on garment 120 is illustrated in accordance with an alternative embodiment of the present invention. The garment 120 is constructed similar to the pull-on garment 20 illustrated in FIG. 1, with the following exceptions. Specifically, the ear panels 45 continuously extend from the corresponding sides of the chassis 41 in the back waist region 28 to the corresponding side edges 240*a* and 240*b* of the chassis 41 in the front waist region 26. Alternatively, the ear panels 45 can continuously extend from the corresponding sides of the chassis 41 in the front waist region 26 to the corresponding side edges of the chassis 41 in the back waist region 28. The side seams 32 each join the chassis 41 and the ear panels 45 along the corresponding side edges 240*a-b* and 242*a-b* to form the two leg openings 34 and the waist opening 36. The side seams 32 can be configured in any manner described above.

Figure 10:
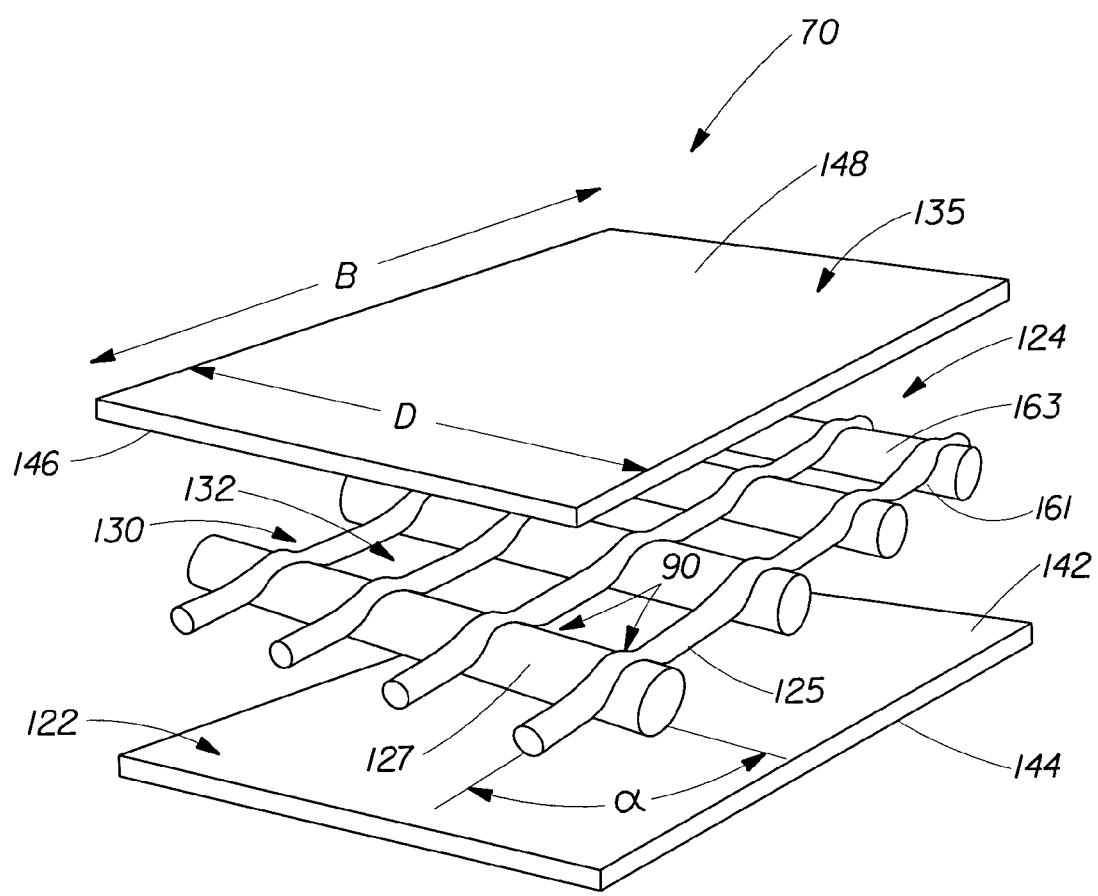
FIG. 10 is an exploded perspective view of an elastic member forming the front and back ear panels illustrated in FIG. 3.

Referring to FIG. 10, the elastic member 70 includes the elastomeric material 124 having a first surface 161 and a second surface 163 opposing the first surface 161, and a first coverstock layer 122 which is joined to the first surface 161 of the elastomeric material 124. In one embodiment, the first coverstock layer 122 is joined to the first surface 161 of the elastomeric material 124 by an adhesive 160 as shown, for example, in FIG. 11. The elastic member 70 can further include a second coverstock layer 135 which is joined to the second surface 163 of the elastomeric material 124 by an adhesive 164.

The elastomeric material 124 may be formed in a wide variety of sizes, forms and shapes. In one embodiment, the elastomeric material 124 is in the form of a continuous plane layer. Suitable forms of a continuous plane layer include a scrim, a perforated (or apertures formed) film, an elastomeric woven or nonwoven, strands of elastics, films that have been processed so as to be extensible as appreciated by one having ordinary skill in the art, and the like. The continuous plane layer may take any shape which can be suitably provided in the ear panels. Suitable shapes of continuous plane layer include a quadrilateral including a rectangle and a square, a trapezoid, and the other polygons. In an alternative embodiment, the elastomeric material 124 is in the form of discrete strands (or strings) which are not connected to each other.

Elastomeric materials which have been found to be especially suitable for the elastomeric material 124 are styrenic block copolymer based scrim materials, perforated (or apertured) elastic films, having a thickness of from about 0.05 mm to about 1.0 mm (0.002 inch-0.039 inch). Other suitable elastomeric materials for the elastomeric material 124 include "live" synthetic or natural rubber, other synthetic or natural rubber foams, elastomeric films (including heat shrinkable elastomeric films), elastomeric woven or nonwoven webs, elastomeric composites, or the like.

Figure 11:
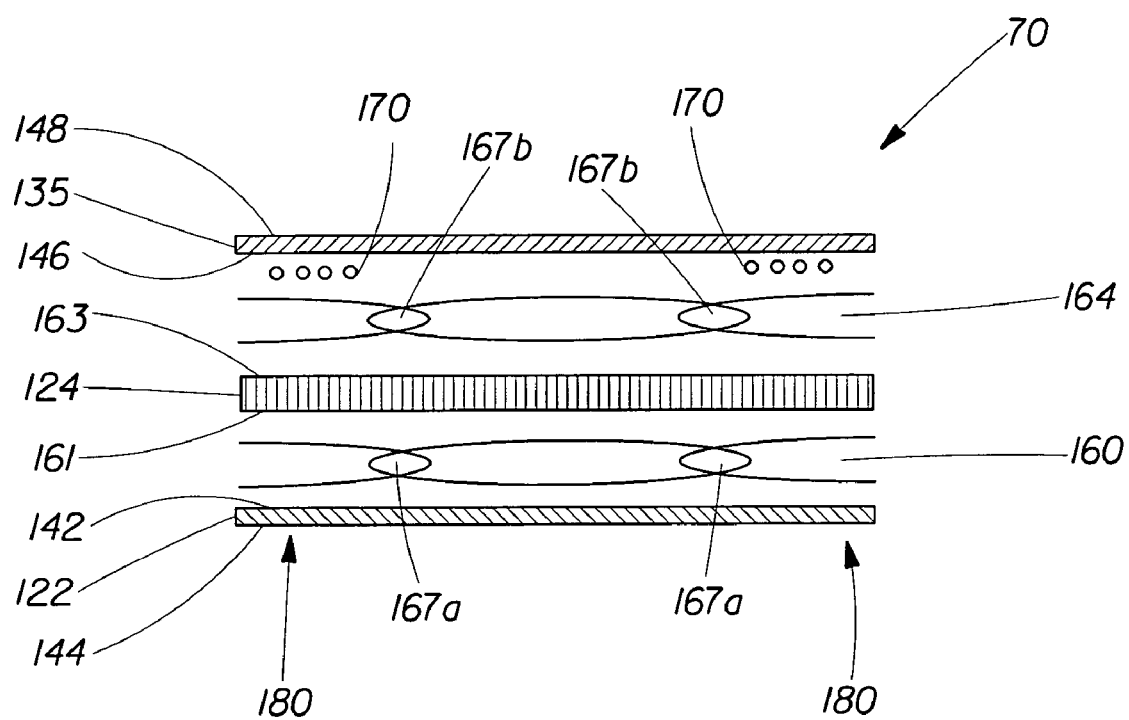
FIG. 11 is a fragmentary enlarged side elevation view of the elastic member shown in FIG. 3.
Figure 13:
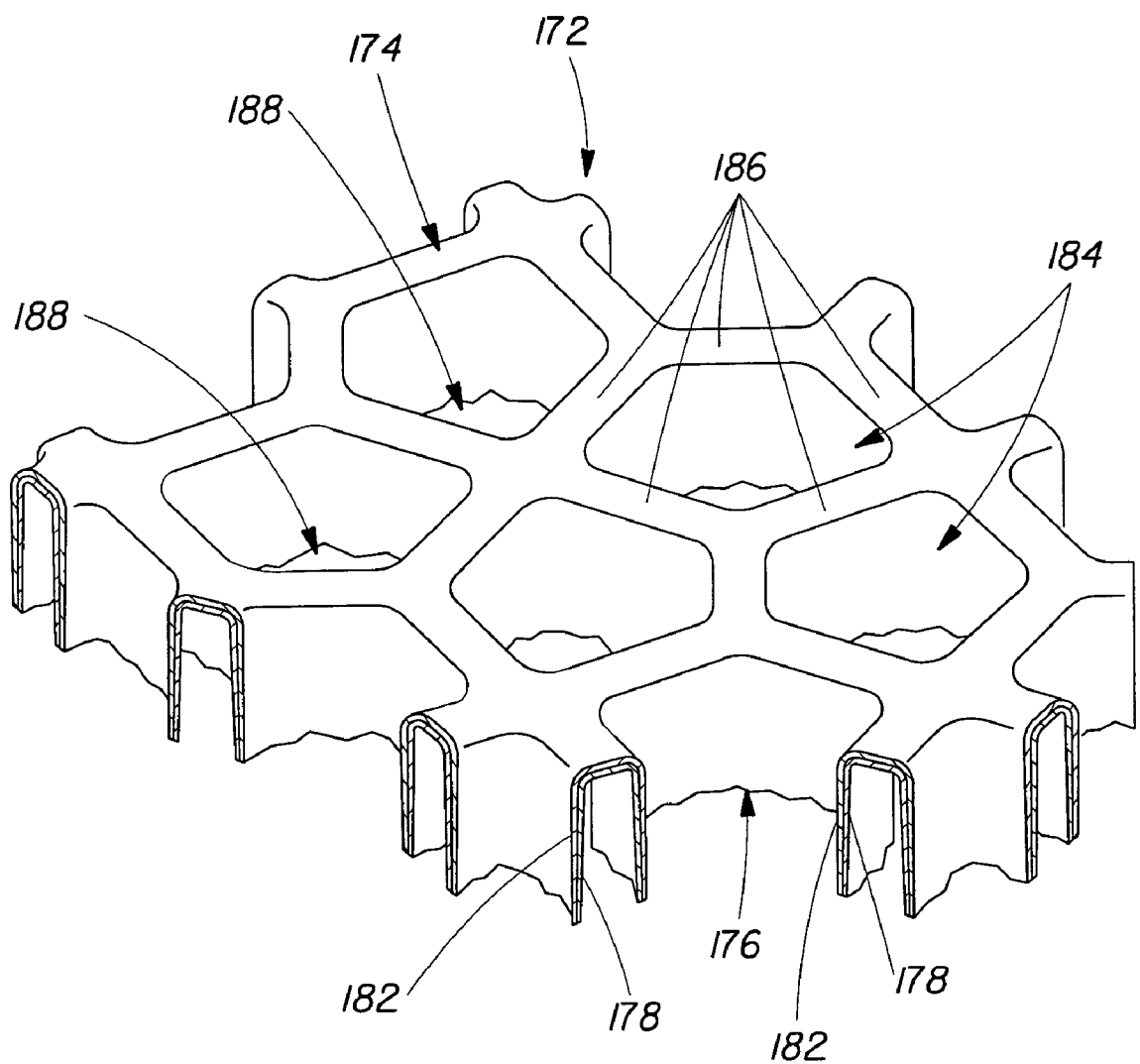
FIG. 13 is a fragmentary enlarged perspective illustration of an elastic material constructed in accordance with an alternative embodiment.

Referring now to FIG. 13, the elastomeric material 124 shown in FIGS. 10 and 11 can be a porous, macroscopically-expanded, three-dimensional elastomeric web 172. The web 172 has a continuous first surface 174 and a discontinuous second surface 176 remote from first surface 174. The elastomeric web 172 comprises a formed film having at least two polymeric layers, with at least one of the layers being an elastomer layer 178 and at least one of the other layers being a substantially less elastomeric skin layer 182. The elastomeric web 172 defines a multiplicity of primary apertures 184 in the first surface 174 of the web 172, the primary apertures 184 being defined in the plane of the first surface 174 by a continuous network of interconnecting members 186. Each interconnecting member 186 exhibits an upwardly concave-shaped cross-section along its length. The interconnecting members 186 terminate substantially concurrently with one another to form a secondary aperture 188 in the plane of the second surface of the web. The primary apertures 184 may define any suitable shape. The detail of such a structure and the method to manufacture is disclosed in U.S. patent application Ser. No. 08/816,106, filed Mar. 14, 1997. A suitable porous elastomeric material 124 is manufactured by the Tredegar Film Products under the designation X-25007.

The extension properties of the side elastomeric material 124 such as the First Cycle Extension Force at 100% Extension (FCEF100%), the First Cycle Extension Force at 200% Extension (FCEF200%), the Second Cycle Recovery Force at 50% Extension (SCRF50%) and sustained load at 50% after 10-12 hours are important considerations in the performance of disposable garments. The side elastomeric material 124 has extension properties within the defined ranges herein. The FCEF100% and the FCEF200% are measures of the overall perceived "stretchiness" during application/removal of disposable garments. These two properties also affect the ability of the applicator to achieve a suitable degree of application stretch. A side elastomeric material 124 with a relatively high FCEF100% and FCEF200% can cause difficulty in applying the disposable garment onto the wearer. On the other hand, a side elastomeric material 124 with a relatively low FCEF100% and FCEF200% may not achieve a suitable level of body fitting/conformity. The SCRF50% also closely relates to the body fitting/conformity of disposable garments for the wearer. A side elastomeric material 124 with a relatively high SCRF50% tends to cause red marking on the skin of the wearer and may be uncomfortable for the wearer during usage. A side elastomeric material 124 with a relatively low SCRF50% may not provide enough elastic force to keep the diaper in place on the wearer or may not provide good body fit. The sustained load at 50% after 10-12 hours evaluates the force decay over time. This force decay should be limited or substantial sagging will result.

The values of FCEF100%, FCEF200% and SCRF50% can be measured by using a tensile tester. The tensile tester includes an upper jaw and a lower jaw which is located below the upper jaw. The upper jaw is movable and is connected to an extension force measuring means. The lower jaw is fixed at a desk (or floor). A test specimen (i.e., the elastomeric material to be measured) which has about 2.54 cm (1.0 inch) in width and about 12.75 cm (5 inches) in length is prepared and clamped between the upper jaw and the lower jaw so that the effective specimen length (L) (i.e., gauge length) is about 5.08 cm (2.0 inches). The extension force is applied to the test specimen through the upper jaw. When no extension force is applied to the test specimen, the test specimen is in its original length (i.e., 0% extension). A tensile tester suitable for use herein is available from Instron Corporation (100 Royall Street, Canton, Mass. 02021, U.S.A.) as Code No. Instron 5564.

Figure 12:
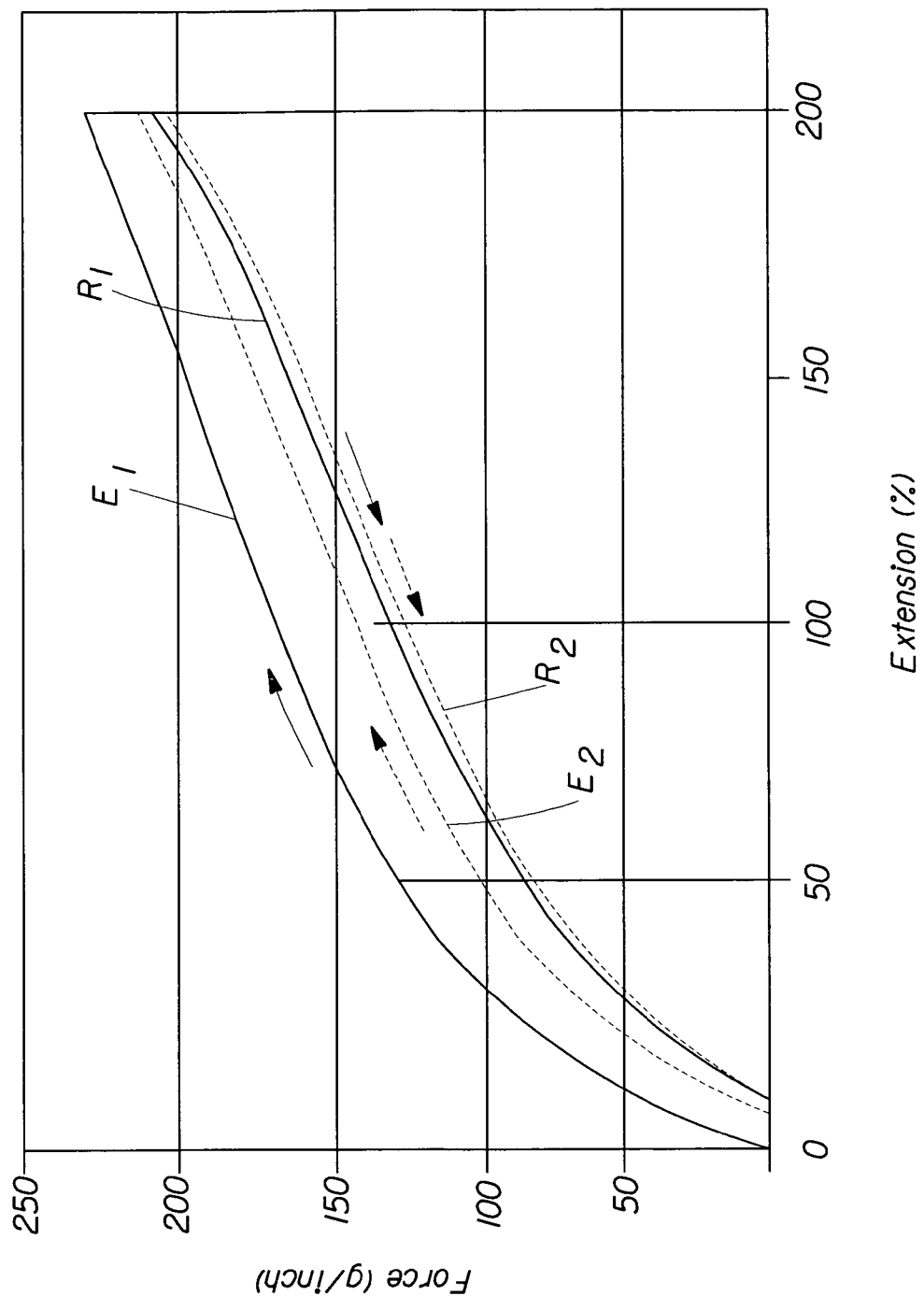
FIG. 12 is a graph showing the two-cycles of hysteresis curves of an elastomeric material in accordance with one aspect of the present invention.

FIG. 12 shows one example of the extension and recovery force curves for the two cycle hysteresis of the elastomeric material 124. The curve E1 shows the extension force in the first cycle, while the curve R1 shows the recovery force in the first cycle. The curve E2 (shown in dashed lines) shows the extension force in the second cycle, while the curve R2 shows the recovery force in the second cycle. The extension and recovery properties are measured as follows.

In the first cycle, the test specimen is subjected to an initial extension force at a crosshead rate of 50.8 cm/min (20 in/min) at about 23.degree. C. and held for 30 seconds at 200% extension. The test specimen is then allowed to relax at the same rate to the original state (i.e., 0% extension). The test specimen is allowed to remain unconstrained for one minute before being subjected to a second extension force (for the second cycle) at the same rate and conditions.

In accordance with certain aspects of the invention, the FCEF 100% of the side elastomeric material 124 is at least about 100 grams/inch. Alternatively, the FCEF100% is between about 120 to about 220 grams/inch, and alternatively still between about 150 grams/inch and 190 grams/inch. The FCEF200% can be between about 160 grams/inch and about 450 grams/inch, alternatively between about 180 grams/inch and about 300 grams/inch, and alternatively still between about 200 grams/inch and about 240 grams/inch. The SCRF50% of the side elastomeric material 124 can be between about 40 grams/inch and about 130 grams/inch, alternatively between about 65 grams/inch and about 105 grams/inch, and alternatively still between about 75 grams/inch and about 95 grams/inch. The sustained load at 50% after 10-12 hours can be between about 40 grams/inch and about 130 grams/inch, alternatively between about 65 grams/inch and about 105 grams/inch, and alternatively still between about 75 grams/inch and about 95 grams/inch.

Referring to FIG. 10, the elastomeric scrim 124 has a plurality of first strands 125 and a plurality of second strands 127. The plurality of first strands 125 intersect the plurality of second strands 127 at nodes 130 at a predetermined angle α . . . , forming a net-like open structure having a lurality of apertures 132. Each aperture 132 is defined by at least two adjacent first strands and at least two adjacent second strands, so that the apertures 132 are substantially rectangular in shape. Other configurations of the apertures 132, such as parallelograms, squares, or circular arc segments, can also be provided. The first and second strands 125 and 127 are substantially straight and substantially parallel to one another. The first strands 125 can intersect the second strands 127 at nodes 130 such that the angle α is about 90 degrees. The first and second strands 125 and 127 are joined or bonded at nodes 90.

A suitable elastomeric scrim 124 is manufactured by the Conwed Plastics Company (Minneapolis, Minn., U.S.A.) under the designation XO2514. This material has about 12 elastic strands per inch in the structural direction B (i.e., the first strands 125) and about 7 elastic strands per inch in the structural direction D (i.e., the second strands 127).

In the embodiment shown in FIG. 10, the elastic member 70 includes first and second coverstock layers 122 and 135, and elastomeric material 124 disposed in the first and second coverstock layers 122 and 135, though it should be appreciated that the elastic member 70 could include additional coverstock layers could be included. The first coverstock layer 122 has an inner surface 142 and an outer surface 144. The inner surface 142 of the first coverstock layer 122 is the surface that is positioned facing the elastomeric material 124. The second coverstock layer 135 also has an inner surface 146 and an outer surface 148. The inner surface 146 of the second coverstock layer 135 is the surface that is positioned facing the elastomeric material 124. The elastomeric material 124 also has two planar surfaces, first surface 161 and second surface 163, each of which is substantially parallel with the planes of the first and second coverstock layers 122 and 135. The first surface 161 is that planar surface of the elastomeric material 124 that is most closely adjacent with the inner surface 142 of first coverstock layer 122. The second surface 163 is that planar surface of elastomeric material 124 that is most closely adjacent to the inner surface 146 of the second coverstock layer 135.

Since the elastic member 70 will be subjected to mechanical stretching before and during use, the first and second coverstock layers 122 and 135 can have a relatively high elongation at breaking, and are more stretchable or elongatable, yet more drawable (but not necessarily elastomeric), without undue (or any), tearing or ripping. Further, the first and second coverstock layers 122 and 135 are compliant, soft feeling, and non-irritating to the wearer's skin and give the article the feel and comfort of a cloth garment. Suitable materials for the first and second coverstock layers 122 and 135 can be manufactured from a wide range of materials such as plastic films, apertured plastic films, woven or nonwoven webs of natural fibers (e.g., wood or cotton fibers), synthetic fibers (e.g., polyolefins, polyamides, polyester, polyethylene, or polypropylene fibers), or a combination of natural and/or synthetic fibers, or coated woven or nonwoven webs.

Each of the first and second coverstock layers 122 and 135 can be an identical consolidated nonwoven material. An exemplary nonwoven material is manufactured by the Fiberweb North America, Inc. (Simpsonville, S.C., U.S.A.) under the designation Sofspan 200. This material has a basis weight of 25 g/m$^2$ before consolidation and a basis weight of about 63 g/m$^2$ after consolidation. Herein, "basis weight" is the weight of one square meter of planar web material. Alternatively, highly strainable nonwoven materials may be used. Alternatively, the first and second coverstock layers 122 and 135 need not be of identical materials, as long as the desired performance requirements, such as elastic performance, softness, flexibility, breathability and durability, are met. Herein, "consolidated nonwoven material" means a nonwoven material that has been gathered or necked under mechanical tension in the structural direction D so that the material can elongate in the structural direction D under low force.

FIG. 11 shows a fragmentary enlarged side view of the elastic member 70, which can be formed as a laminate. It has been found that when the elastic member 70 is bonded or otherwise anchored such that side anchor zones A are created, the elasticity of the elastic member 70 is increased, and the elastic member 70 is substantially free from delamination and creep, while providing very good performance characteristics in all performance categories with no trade-offs between any performance characteristics required. The side anchoring can be performed by side gluing with adhesive beads to anchor the elastomeric material 124 between the coverstock layers 122 and 135 as a part of the lamination process. Alternatively, side anchoring may be performed by sewing, heat sealing, ultrasound bonding, needle punching, alternative gluing processes, embossing pressure bonds or by any other means known to those skilled in the art. Another alternative is to side anchor the layers of the laminate structure after the lamination of the elastomeric and coverstock components has been performed.

The elastic member can particularly provide very good soft feel for the wearer and for the consumer. This is important because consumers value softness. In conventional laminates, the attempts to eliminate creep have frequently required an unacceptable decrease in softness, often accompanied by an unacceptable decrease in an ability to activate. This is because such previous attempts (which have fallen short of eliminating creep) have focused on the application of additional melt blown adhesive, often in an overall coating pattern, in the attempt to strengthen the bonds. This has generally resulted in an undesirable overall stiffening of the laminate. However, the laminates described herein provide elimination of creep without the loss of consumer-desired soft feel and without compromise of activation ability.

Referring to FIG. 11, a first adhesive 170 is applied to the inner surface 146 of the second coverstock layer 135 in positions that correspond to each of the outer edges 180 of the elastic member 70. The first adhesive 170 may alternatively or additionally be applied to the inner surface 142 of the first coverstock layer 122. For ease of illustration, the description and figures refer to application to the second coverstock layer 135 only.

This pattern creates side anchor zones A, which substantially eliminate the delamination and creep associated with previously known laminates and which allows the elastic member 70 to experience higher strains without creeping or delaminating. It has also been found that confining the first adhesive 170 to the edge areas 180 of the elastic member 70 avoids impeding the extensibility of the elastic member 70 and also avoids tears in the coverstock layers 122 and 135. The first adhesive 170, which is a flexible adhesive with an amorphous and crystallizing component, is applied as a plurality of beads, as shown in FIG. 11. Such an adhesive is made by Nitta Findley Co., Ltd., Osaka, Japan, under the designation H9224.

The elastic member 70 can include a second adhesive 164, which is preferably applied to the second surface 163 of the elastomeric material 124, but could alternatively be applied to the first surface 161 of the elastomeric material 124. The second adhesive 164 is applied in a spiral spray pattern, thereby forming bond points 167b that are more discrete than would be formed by a linear spray application. Without being bound by theory, it is believed that most of the second adhesive 164 is sprayed in the structural direction D (see FIG. 10). Thus, it has been found that spiral spraying results in very good activation properties. Herein, "activation" refers to the ability to stretch.

It has been found that spraying the layer of second adhesive 164 directly onto the second surface 163 of the elastomeric material 124 is more preferable than applying the second adhesive 164 to the opposing (i.e., second) coverstock layer 135. This is because the second adhesive 164 tends to penetrate through any residual processing agents or oils that may remain on the surface of the elastomeric material 124. Such residual materials, if left to remain on the elastomeric material 124, may weaken the adhesive bonds and thus the elastic member 70 over time. For example, if these residual materials are left intact, the bonds used to form the elastic member 70 may weaken during the time interval prior to consumer purchase of the product.

Peel values for the elastic member 70 in the spiral adhesive areas are typically higher when the adhesive 164 is applied directly to the elastomeric material 124 rather than to the opposing (i.e., second) coverstock layer 135. Herein, "peel value" refers to the amount of force required to separate the two layers of coverstock material, 122 and 135, from each other. Higher peel values typically equate to less chance of delamination in use.

A third adhesive 160, which can be the same elastomeric adhesive as the second adhesive 164, can also be applied to the inner surface 142 of the first coverstock layer 122. In a manner similar to that described with reference to the second adhesive 164 application, the third adhesive 160 is applied in a spiral spray pattern, thereby forming bond points 167a that are more discrete than would be formed by a linear spray application. Without being bound by theory, it is believed that most of the first adhesive 160 so sprayed aligns in the structural direction D. A suitable adhesive for use in the second and third adhesive spiral sprays 162 and 166 is made by Nitta Findley Co., Ltd., Osaka, Japan, under the designation H2120. The add-on level for each of the second and third adhesive sprays 164 and 160 is about 4 to about 12 milligrams per square inch, and alternatively about 8 milligrams per square inch.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean about 40 mm.

All documents cited in the Detailed Description of the invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and the scope of the invention. It is therefore intended to cover in the appended claims all such changes and modifications that are within the scope of this invention.

What is claimed is:

1. A disposable preformed pant-type garment defining a front waist region, a back waist region, and a crotch region disposed between the front waist region and the back waist region, the garment comprising:

a chassis defining laterally opposing first and second side edges extending along the front waist region, the crotch region, and the back waist region, wherein at least one of the side edges is joined to itself by a single use breakable seam disposed on ear panels between the front and back waist regions, respectively, to form a closed side interface defining a leg opening located at a lower end of the closed side interface, and at least partially defining a waist opening at an upper end of the closed side interface; and an unseamed gap extending a distance between 4 mm and 50 mm substantially downward from the waist opening along a direction of elongation defined by the closed side interface.

2. The disposable garment as recited in claim 1, further comprising a tab member extending from the joined side edge proximal the upper end of the closed side interface.

3. The disposable garment as recited in claim 2, wherein the tab member is disposed at a middle portion location of the closed side interface.

4. The disposable garment as recited in claim 2, wherein the closed side interface includes a substantially unbonded region in alignment with the tab member.

5. The disposable garment as recited in claim 2, wherein the seam comprises an initiation region at least partially aligned with the tab member, and a propagation region disposed below the initiation region.

6. The disposable garment as recited in claim 5, wherein the initiation region is substantially unbonded.

7. The disposable garment as recited in claim 5, wherein the tab member is wholly aligned with the initiation region.

8. The disposable garment as recited in claim 5, wherein the propagation region has a resistance to a user-applied opening force, wherein the resistance is greater than that of the initiation region.

9. The disposable garment as recited in claim 1, wherein the tab member extends horizontally from the joined side edge.

10. The disposable garment as recited in claim 1, wherein the chassis further defines a back waist edge and a front waist edge both extending from the joined side edge.

11. The disposable garment as recited in claim 10, wherein the tab member extends vertically from at least one of the back waist edge and the front waist edge, and wherein the tab member is substantially in vertical alignment with the seam.

12. The disposable garment as recited in claim 1, wherein the seam comprises hook-and-loop fasteners.

13. The disposable garment as recited in claim 1, wherein the chassis defines a waist edge that, in turn, at least partially defines the waist opening, and wherein a vertical distance within the range of 0 and 10 mm separates the tab from the waist edge.

14. The disposable garment as recited in claim 1, wherein the unseamed gap extends distance between 8 mm and 50 mm substantially downward from the waist opening along the direction of elongation defined by the closed side interface.

15. A disposable preformed pant-type garment defining a front waist region, a back waist region, and a crotch region disposed between the front waist region and the back waist region, the garment comprising:

a chassis defining laterally opposing first and second side edges extending along the front waist region, the crotch region, and the back waist region; and wherein at least one of the side edges is joined to itself by a single use breakable seam disposed on ear panels between the front and back waist regions, respectively, to form a closed side interface defining a leg opening located at a lower end of the closed side interface, and at least partially defining a waist opening at an upper end of the closed side interface, wherein the seam comprises an initiation region and a propagation region, wherein the initiation region and propagation each have a resistance to a user-applied opening force, wherein the resistance of the initiation region is less than the resistance of the propagation region.

16. The disposable garment as recited in claim 15, wherein the initiation region defines a vertical distance ratio within a range of 4:96 and 35:65 relative to the propagation region.

17. The disposable garment as recited in claim 16, wherein the ratio is within the range of 4:96 and 20:80.

18. The disposable garment as recited in claim 15, wherein the initiation region is unbonded.

19. The disposable garment as recited in claim 15, wherein the initiation region is bonded.

20. The disposable garment as recited in claim 19, wherein the initiation region includes a bonded portion adjacent to the waist opening, and an unbonded gap between the bonded portion and the propagation region.

21. The disposable garment as recited in claim 15, wherein the seam further comprises a leading region disposed between the initiation region and the propagation region, wherein the leading region has a resistance to the user-applied opening force, wherein the resistance of the leading edge is greater than that of the propagation region.

22. The disposable garment as recited in claim 21, wherein the seam further comprising a completion region disposed between the propagation region and the leg opening, wherein the completion region has a resistance to the user-applied opening force, wherein the resistance of the completion region is less than that of the propagation region.

23. The disposable garment as recited in claim 22, wherein the completion region is unbonded.

24. The disposable garment as recited in claim 22, wherein the seam further comprises a trailing region disposed between the propagation region and the completion region, wherein the trailing region has a resistance to the user-applied opening force, wherein the resistance of the trailing region is greater than that of the propagation region.

25. The disposable garment as recited in claim 24, wherein the resistance of the trailing region is less than that of the leading region.

26. The disposable garment as recited in claim 24, wherein the tab member is located proximal a middle portion of the closed side interface.

27. The disposable garment as recited in claim 15, further comprising a tab member extending from the closed side interface.

28. The disposable garment as recited in claim 27, wherein the tab member is at least partially aligned with the initiation region.

29. The disposable garment as recited in claim 27, wherein the initiation region comprises the tab member.

30. The disposable garment as recited in claim 27, wherein the tab member is located proximal an upper end of the closed side interface.

31. The disposable garment as recited in claim 27, wherein the tab member is located proximal a lower portion of the closed side interface.

32. The disposable garment as recited in claim 15, wherein the initiation region is disposed between a pair of propagation regions.

33. The disposable garment as recited in claim 32, wherein at least one of the propagation regions comprise interlocking hooks and loops.

34. The disposable garment as recited inc claim 32, further comprising a tab member extending from the closed side interface and at least partially aligned with the initiation region.

35. A disposable preformed pant-type garment defining a front waist region, a back waist region, and a crotch region disposed between the front waist region and the back waist region, the garment comprising:
- a chassis defining laterally opposing first and second side edges extending along the front waist region, the crotch region, and the back waist region; and
- wherein at least one of the side edges is joined to itself by a single use breakable seam disposed on ear panels between the front and back waist regions, respectively, to form a closed side interface defining a leg opening located at a lower end of the closed side interface, and at least partially defining a waist opening at an upper end of the closed side interface disposed above the lower end;
- a tab member extending from the closed side interface; and
- indicia disposed on the tab member and visible to the user, wherein the indicia communicate usage of the tab member to the user.

36. The disposable garment as recited in claim 35, wherein the indicia comprises an arrow.

37. The disposable garment as recited in claim 35, wherein the indicia comprises a color that is different from that of surrounding garment components.

38. The disposable garment as recited in claim 35, wherein the indicia comprises lettering.

39. The disposable garment as recited in claim 35, wherein the indicia comprises a hand graphic.

40. The disposable garment as recited in claim 35, wherein the indicia is printed on the tab.

41. The disposable garment as recited in claim 35, wherein the indicia is disposed on an auxiliary layer that is attached to the tab member.

42. A disposable preformed pant-type garment defining a front waist region, a back waist region, and a crotch region disposed between the front waist region and the back waist region, the garment comprising:
- a chassis defining laterally opposing first and second side edges extending along the front waist region, the crotch region, and the back waist region; and
- wherein at least one of the side edges is joined to itself by a single use breakable seam disposed on ear panels between the front and back waist regions, respectively, to form a closed side interface defining a leg opening located at a lower end of the closed side interface, and at least partially defining a waist opening at an upper end of the closed side interface, wherein the seam comprises an initiation region and a propagation region, wherein the initiation region and propagation each have a resistance to a user-applied opening force, wherein the resistance of the initiation region is less than the resistance of the propagation region, and wherein the closed side interface is configured to open along the seam in response to the user-applied opening force.

43. The disposable garment as recited in claim 42, wherein the closed side interface is configured to open only along the seam in response to the user-applied opening force.

44. The disposable garment as recited in claim 42, wherein the seam equally divides the closed side interface.

45. The disposable garment as recited in claim 42, wherein the initiation region and the propagation region together form a linear seam that is bonded at substantially uniform intervals.

46. The disposable garment as recited in claim 42, wherein the initiation region and the propagation region together form a linear seam that is substantially continuously bonded.

* * * * *